US010689684B2

(12) United States Patent
Chen et al.

(10) Patent No.: US 10,689,684 B2
(45) Date of Patent: Jun. 23, 2020

(54) MODIFICATIONS TO POLYNUCLEOTIDES FOR SEQUENCING

(71) Applicants: Microsoft Technology Licensing, LLC, Redmond, WA (US); University of Washington, Seattle, WA (US)

(72) Inventors: Yuan-Jyue Chen, Seattle, WA (US); Karin Strauss, Seattle, WA (US); Luis H. Ceze, Seattle, WA (US); Lee Organick, Seattle, WA (US); Randolph Lopez, Seattle, WA (US); Georg Seelig, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 572 days.

(21) Appl. No.: 15/431,897

(22) Filed: Feb. 14, 2017

(65) Prior Publication Data

US 2018/0230509 A1    Aug. 16, 2018

(51) Int. Cl.
  *C12Q 1/6806* (2018.01)
  *C12Q 1/6869* (2018.01)
  *G16B 30/00* (2019.01)

(52) U.S. Cl.
  CPC ......... *C12Q 1/6806* (2013.01); *C12Q 1/6869* (2013.01); *G16B 30/00* (2019.02)

(58) Field of Classification Search
  None
  See application file for complete search history.

(56) References Cited

U.S. PATENT DOCUMENTS

| 8,404,828 | B2 | 3/2013 | Kakol et al. |
| 8,889,348 | B2 | 11/2014 | Ju |
| 9,150,918 | B2 | 10/2015 | Turner et al. |
| 2015/0261664 | A1 | 9/2015 | Goldman et al. |
| 2015/0275289 | A1 | 10/2015 | Otwinowski et al. |
| 2015/0284769 | A1 | 10/2015 | Schroeder |
| 2016/0110498 | A1 | 4/2016 | Bruand et al. |
| 2016/0378916 | A1 | 12/2016 | Drmanac et al. |
| 2018/0253528 | A1 | 9/2018 | Strauss et al. |

FOREIGN PATENT DOCUMENTS

| CN | 104850760 | A | 8/2015 |
| CN | 105022935 | A | 11/2015 |
| IN | 02406CH2010 | A | 11/2012 |
| WO | 2015057985 | A1 | 4/2015 |
| WO | 2016154540 | A1 | 9/2016 |

OTHER PUBLICATIONS

Shendure et al. Next-generation DNA sequencing Nature Biotechnology vol. 26, pp. 1135-1145 (Year: 2008).*
"A Paradigm Shill in Biology that Can Advance all Industries", Retrieved from: https://web.archive.org/web/20160809224734/http://synthorx.com/applications, Aug. 9, 2016, 1 Page.
"Expanding the Genetic Code with Synthetic Bases", Retrieved From: http://epigenie.com/expanding-the-genetic-code-with-synthetic-bases/, Jul. 27, 2015, 3 Pages.
"IDC, Where in the World is Storage", Retrieved From: http://www.idc.com/downloads/where_is_storage_infographic_243338.pdf, Mar. 8, 2017, 1 Page.
Batu, et al., "Reconstructing Strings from Random Traces", Proceedings of the Fifteenth Annual ACM-SIAM symposium on Discrete algorithms, Jan. 11, 2004, 9 Pages.
Blawat, et al., "Forward Error Correction for DNA Data Storage", In Proceedings of the International Conference on Computational Science, Jan. 1, 2016, pp. 1011-1022.
Bornholt, "A DNA-Based Archival Storage System", In Proceedings of 21th ACM International Conference on Architectural Support for Programming Languages and Operating Systems, Apr. 2, 2016, 13 Pages.
Carr, Katie, "Milenkovic Looks for Big Data Storage Solution in Dna Storage", Retrieved From: https://www.ece.illinois.edu/newsroom/article/9755, Oct. 29, 2014, 4 Pages.
Church, et al., "Next-Generation Digital Information Storage in DNA", In Journal of Science, vol. 337, Aug. 16, 2012, 2 Pages.
Erlich, et al., "Capacity-Approaching DNA Storage", Retrieved From: https://www.biorxiv.org/content/biorxiv/early/2016/09/09/074237.2.full.pdf, Sep. 9, 2016, 36 Pages.
Erlich, et al., "DNA Fountain Enables a Robust and Efficient Storage Architecture", Retrieved From: https://science.sciencemag.org/content/355/6328/950, Mar. 3, 2017, 4 Pages.
Extance, Andy, "How DNA Could Store all the World's Data", Retrieved From: http://www.nature.com/news/how-dna-could-store-all-the-world-s-data-1.20496, Sep. 2, 2016, 9 Pages.
Goela, et al., "Encoding Movies and Data in DNA Storage", In Proceedings of Information Theory and Applications Workshop (ITA), Jan. 31, 2016, 1 Page.
Goldman, et al., "Towards Practical, High-Capacity, Low-Maintenance Information Storage in Synthesized DNA", In Journal of Nature, vol. 494, Feb. 7, 2013, 4 Pages.
Grass, et al., "Robust Chemical Preservation of Digital Information on DNA in Silica with Error-Correcting Codes", In Publication of Angewandte Chemie International Edition, Feb. 16, 2005, pp. 2552-2555.

(Continued)

*Primary Examiner* — John S Brusca
(74) *Attorney, Agent, or Firm* — Newport IP, LLC; Benjamin A. Keim

(57) ABSTRACT

This disclosure describes techniques to improve the sequencing of polynucleotides by decreasing the likelihood of errors occurring during a sequencing calibration process. In implementations, regions of polynucleotides that are used for the calibration process can be modified to reduce a number of polynucleotides that have a same nucleotide at one or more positions of the calibration regions. In some cases, the calibration regions can be modified by adding a sequence to the polynucleotides that replaces the original calibration regions. Also, the calibration regions can be modified by rearranging the nucleotides at the different positions of the calibration regions. Additionally, the calibration regions can be modified by adding sequences of varying length to the polynucleotides being sequenced to produce polynucleotides having varying length with different calibration regions.

20 Claims, 7 Drawing Sheets

(56) References Cited

OTHER PUBLICATIONS

Kosuri, et al., "Large-Scale De Novo DNA Synthesis: Technologies and Applications", In Journal of Nature Methods, vol. 11, Issue 5, May 2014, pp. 499-507.

Martineau, Kim, "Researchers Store Computer Operating System and Short Movie on DNA", Retrieved From: http://datascience.columbia.edu/researchers-store-computer-operating-system-dna, Mar. 2, 2017, 2 Pages.

Mitra, et al., "Strategies for Achieving High Sequencing Accuracy for Low Diversity Samples and Avoiding Sample Bleeding Using Illumina Platform", In Journal of PLOS One, Apr. 10, 2015, pp. 1-21.

Schreiber, et al., "Analysis of Nanopore Data using Hidden Markov Models", Retrieved From: https://academic.oup.com/bioinformatics/article-abstract/31/12/1897/213759, Feb. 3, 2015, 9 Pages.

Wilson, et al., "Sequence Verification of Synthetic DNA by Assembly of Sequencing Reads", In Journal of Nucleic Acids Research, vol. 41, Issue 1, Oct. 4, 2012, pp. 1-11.

Xu, et al., "Design of 240,000 Orthogonal 25mer DNA Barcode Probes", In Proceedings of the National Academy of Sciences, vol. 106, Issue 7, Feb. 17, 2009, pp. 2289-2294.

Yazdi, et al., "A Rewritable, Random-Access DNA-Based Storage System", In Journal of Scientific Reports, vol. 5, Sep. 18, 2015, 10 Pages.

Yazdi, et al., "DNA-Based Storage: Trends and Methods", Retrieved From: http://www.ntu.edu.sg/home/hmkiah/docs/papers/DNACodes_Survey.pdf, Jul. 2015, 20 Pages.

Yazdi, et al., "Portable and Error-Free DNA-Based Data Storage", Retrieved From: http://biorxiv.org/content/early/2016/10/05/079442, Jan. 2016, pp. 1-4.

Zadeh, et al., "Software News and Updates NUPACK: Analysis and Design of Nucleic Acid Systems", In Journal of Computational Chemistry, vol. 32, Jan. 2015, pp. 170-173.

\* cited by examiner

MODIFICATIONS TO POLYNUCLEOTIDES FOR SEQUENCING

BACKGROUND

Sequencing of polynucleotides relates to determining the arrangement of individual nucleotides in the polynucleotides. Polynucleotides can include sequences of nucleotides arranged in a linear chain of organic molecules that are nitrogen-containing bases, such as adenine (A), guanine (G), thymine (T), cytosine (C), in the case of deoxyribonucleic acid (DNA) and A, G, C, and uracil (U), in the case of ribonucleic acid (RNA). Polynucleotides can be naturally-occurring or synthetic. In some cases, individual nucleotides included in a polynucleotide can pair with a complementary nucleotide in another polynucleotide to produce a double stranded arrangement of polynucleotides. For example, in the case of DNA, T's and A's are complementary and G's and C's are complementary. In the case of ribonucleic acid (RNA), A's and U's are complementary and G's and C's are complementary.

To determine whether a sequencing machine is operating according to specified parameters, a calibration process can take place. The calibration process can include reading one or more nucleotides in a region of at least a portion of the polynucleotides being sequenced. The region of the polynucleotides used during the calibration process can be referred to herein as a "calibration region." In situations where errors occur during calibration, the sequencing machine can stop the sequencing process. In some cases, the errors that occur during sequencing are not related to improper functioning of the sequencing machine, but the errors can be related to the polynucleotides being sequenced. Overcoming the problems that occur during the calibration process where the composition of the polynucleotides contribute to errors can introduce efficiencies into the sequencing process.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Artificially synthesized DNA molecules, such as DNA molecules synthesized to store binary data, may have regions with uneven distributions of nucleotides. Some conventional sequencing machines may fail to properly calibrate if this is the case. To minimize errors that occur during the sequencing calibration process, and thus also minimize later base calling errors, the calibration regions of the polynucleotides can be modified. In some cases, the modifications to the calibration regions can take place before the synthesis of the polynucleotides. In these situations, data corresponding to the polynucleotides can be analyzed for errors that may occur during the sequencing calibration process and the data can be modified to indicate the modified polynucleotides with modified calibration regions. In other situations, the modifications to the polynucleotides can take place after the polynucleotides have been synthesized. In particular implementations, the arrangement of nucleotides included in the calibration regions of polynucleotides can be modified to reduce the likelihood of an error occurring during the calibration process due to the arrangement of the nucleotides included in the polynucleotides being sequenced. In illustrative examples, to reduce the likelihood that errors may occur during a calibration process, the calibration regions of polynucleotides can be modified such that a number of polynucleotides having a same nucleotide at one or more positions of the calibration regions is less than a threshold number.

In various implementations described herein, the calibration regions of polynucleotides can be modified by adding sequences of nucleotides to the polynucleotides being sequenced to produce modified polynucleotides having modified calibration regions. In some cases, the entire original calibration region can be replaced with a new calibration region, while in other situations, a portion of the original calibration region can be replaced to produce a modified calibration region. In this way, the positions of the nucleotides in the original calibration region are shifted and instead of the sequencing machine reading the nucleotides of the original calibration region during the calibration process, the sequencing machine can first read the nucleotides added to the polynucleotides before reading the nucleotides of the original calibration region. The sequences added to the calibration regions can be designed such that the number of polynucleotides being sequenced that have a same nucleotide in one or more positions of the modified calibration regions is less than a threshold number.

In additional examples, the sequences of nucleotides in the calibration regions can be re-ordered or replaced without adding any nucleotides to the polynucleotides being sequenced. In these cases, a mapping between the original sequence of a calibration region and a new sequence of a modified calibration region is stored in order to reproduce the sequence of the original calibration region after the sequencing process has been completed. The modified sequences of the calibration regions can be designed such that the number of polynucleotides being sequenced that have a same nucleotide in one or more positions of the modified calibration regions is less than a threshold number.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
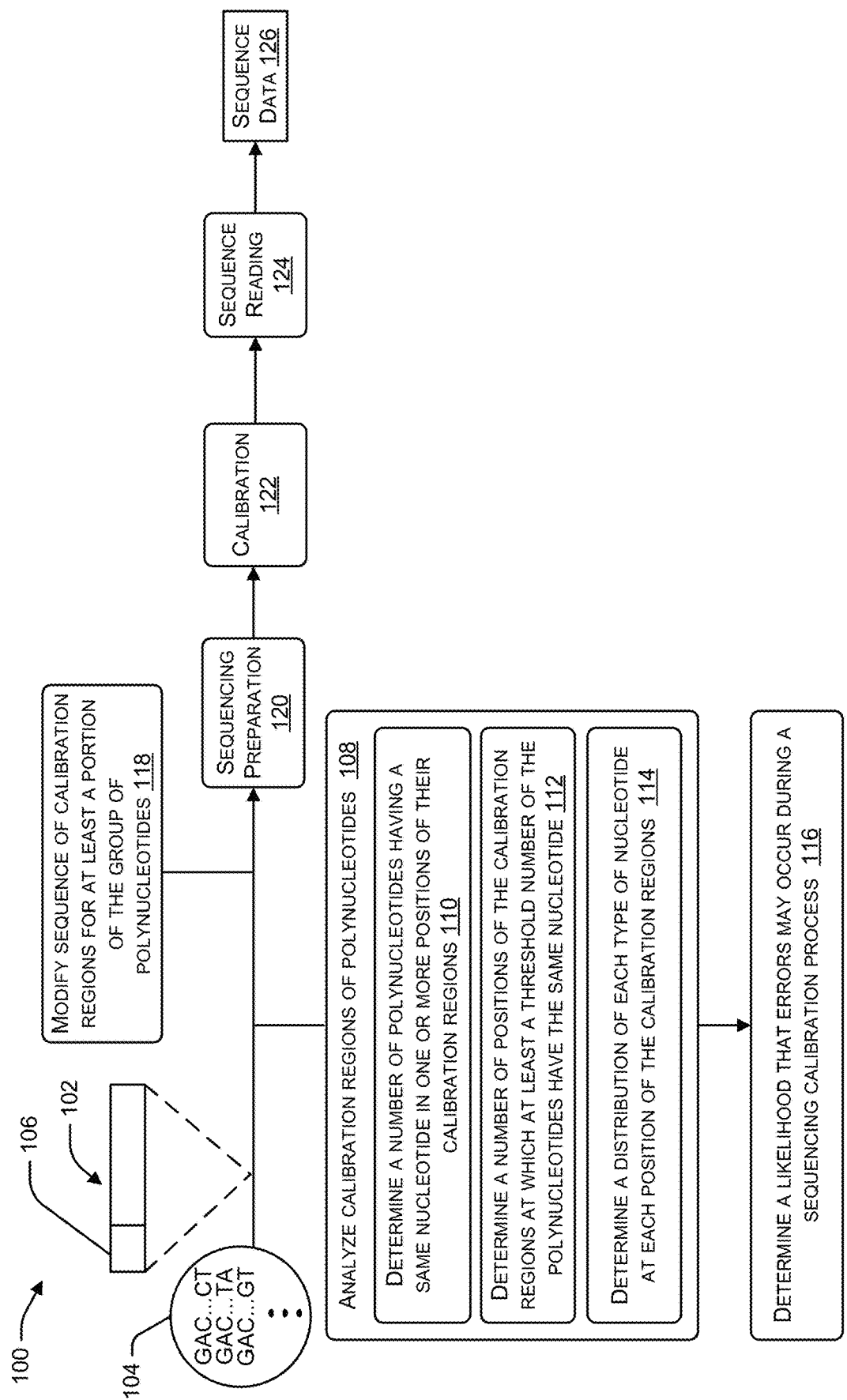
FIG. 1 shows a schematic representation of an example process to modify calibration regions of polynucleotides that are to be sequenced.

This disclosure describes techniques to improve the sequencing of polynucleotides. The techniques described herein can apply to sequencing processes utilized by a number of different sequencing machines. In some cases, the techniques described herein can be applied to sequencing machines that utilize sequencing by synthesis processes. In these particular situations, sequencing can take place by binding polynucleotides to a surface of a flow cell. Polynucleotides can be bound to the surface of a flow cell by attaching sequences referred to herein as adapters to the polynucleotides. An adapter can include a sequence of nucleotides that can bind to complementary sequences on the surface of the flow cell that is used in the sequencing process. The adapters are added to polynucleotides such that each polynucleotide binds to a different location on the surface of the flow cell. In particular implementations, after polynucleotides attach to the surface of a flow cell via the adapters, the polynucleotides can be replicated and amplified. A polymerase chain reaction (PCR) can be used to replicate and amplify polynucleotides during sequencing. Amplifying and replicating the polynucleotides can produce clusters of each polynucleotide at different locations of the flow cell. The amplification process can produce an amplification product that includes many copies of the polynucleotide. As used herein, amplification of polynucleotides can refer to an exponential increase in the number of copies of the polynucleotide.

Sequencing can also include adding fluorescently labeled nucleotides to the polynucleotides in the clusters of the flow cell. The fluorescently labeled nucleotides can be added using a sequencing primer that has been added to a complementary region of each polynucleotide to be sequenced. Each type of nucleotide found in DNA, or RNA in some situations, can be coupled to a different fluorophore using a cleavable bond. For example, each type of nucleotide, G, C, A, T, or U in the case of RNA, can be associated with a respective fluorophore. The different fluorophores coupled to the nucleotides can emit electromagnetic radiation at different wavelength distributions. The different wavelength distributions of the fluorophores can be associated with different colors. For example, a first fluorophore can emit electromagnetic radiation at a first set of wavelengths and a second fluorophore can emit electromagnetic radiation at a second set of wavelengths. The first set of wavelengths can be different from the second set of wavelengths, although, in some cases, the first set of wavelengths and the second set of wavelengths can have some overlap. In some situations, one type of nucleotide may not be bound to a respective fluorophore and this type of nucleotide can be detected based on the absence of radiation emission.

Sequencing by synthesis can take place over a number of rounds with each round determining the nucleotides located at a particular position of the sequences of the polynucleotides being sequenced. During each round of sequencing, a single fluorophore-bound nucleotide is added to a complementary nucleotide of each polynucleotide. The polynucleotides are then exposed to electromagnetic radiation, such as via a laser. Upon excitation by the electromagnetic radiation, the fluorophores attached to the nucleotides that have been added emit electromagnetic radiation having certain wavelengths. A camera can capture images of the flow cell during the application of electromagnetic radiation and the images can include regions of illumination for each polynucleotide. The regions of illumination can be associated with different colors based on the nucleotide at a respective position of the polynucleotides. Thus, the images can be analyzed using machine-vision techniques to determine which portions of the captured images correspond to clusters of polynucleotides based on the location of illumination and the wavelengths emitted by the various fluorophores. For example, clusters emitting at a first distribution of wavelengths (e.g., wavelengths corresponding to a red color) can be associated with a first type of nucleotide (e.g., thymine) and clusters emitting at a second distribution of wavelengths (e.g., wavelengths corresponding to a green color) can be associated with a second type of nucleotide (e.g., guanine). Sequence diversity between the various clusters bound to the flow cell results in a diversity of colors emitted by the fluorophores and detected by the camera. By continuing to add complementary fluorophore-bound nucleotides to the polynucleotides being sequenced, applying electromagnetic radiation, and analyzing images of the flow cell, the arrangement of nucleotides for each polynucleotide can be determined.

To determine whether a sequencing machine that utilizes sequencing by synthesis is operating according to specified parameters, a calibration process can take place. In some cases, the calibration process analyzes images captured by the camera to identify the locations of each individual cluster on the flow cell. When two adjacent clusters are different colors it is easier to distinguish the separate cluster boundaries than when the adjacent clusters are the same color. The calibration process can include reading a certain number of consecutive nucleotides at the beginning of each polynucleotide being sequenced in order to locate the clusters on the flow cell. The region of the polynucleotides used during the calibration process can be referred to herein as a "calibration region." The sequencing machine typically expects to detect about an equal distribution for each type of nucleotide for a given round of sequencing because this ratio of nucleotides is common in naturally occurring DNA. Equal distribution of nucleotides at a given position among all the DNA molecules bound to a flow cell increases the probability that adjacent clusters will have different colors and be distinguishable from one another. To illustrate, for DNA, the sequencing machine can expect to determine that about 25% of clusters will be associated with A, about 25% of clusters will be associated with T, about 25% of clusters will be associated with G, and about 25% of clusters will be associated with C.

In situations where errors occur during calibration, the sequencing machine can stop the sequencing process. In some cases, the errors that occur with respect to sequencing machines that utilize sequencing by synthesis processes are related to the arrangements of nucleotides in the calibration regions of the polynucleotides being sequenced. For example, an error can occur during the calibration process when the expected distribution of each type of nucleotide at one or more positions of the calibration region falls outside of a specified range for each type of nucleotide. In particular instances, errors can occur in situations where more than a threshold number of polynucleotides have a same nucleotide at a same position. In these cases, the sequencing machine may be unable to process the image of the flow cell because the regions of illumination associated with too many clusters may be the same color and, absent a color difference, it is difficult to distinguish two different clusters that partially overlap. Thus, the sequencing machine is unable to distinguish between the regions of illumination for individual clusters of target polynucleotides and is therefore unable to determine the nucleotides associated with the individual clusters during subsequent base calling. In some instances, this can be referred to as "overclustering."

Conventional techniques used to minimize calibration errors can reduce the concentration of polynucleotides having the same nucleotide at one or more positions of the calibration region. In some cases, the number of polynucleotides being sequenced can be reduced such that the clusters of the polynucleotides will be spaced far enough apart that even if greater than a threshold concentration of polynucleotides have the same nucleotide at one or more positions, the illumination regions produced during sequencing will not overlap. Thus, the sequencing machine can identify the individual clusters of the polynucleotides on the flow cell. In other situations, an amount of known polynucleotides that have the requisite distribution of each type of nucleotide in the calibration region can be sequenced along with the target polynucleotides. In this way, a sufficient number of the known polynucleotides can be interspersed on the flow cell with the target polynucleotides to minimize overlap between the illumination regions of the polynucleotides being sequenced. These conventional techniques suffer from the drawback of decreasing throughput because the number of actual target polynucleotides being sequenced is reduced.

In particular implementations, this disclosure describes techniques to improve the sequencing of polynucleotides being sequenced by sequencing machines that utilize sequencing by synthesis processes. For example, the techniques described herein can improve sequencing of a group of polynucleotides that includes at least a threshold number of polynucleotides having one or more positions at the 5' and/or 3' ends with a same nucleotide. In some implementations, the positions at the 5' and/or 3' ends of the polynucleotides can comprise a calibration region that is used by a sequencing machine during a calibration process. In situations where at least a threshold number of polynucleotides have one or more positions of their calibration regions with a same nucleotide, errors can occur during the calibration process. In particular implementations, the systems and processes described herein can be utilized to minimize errors that can occur during the calibration process implemented by sequencing machines that utilize techniques that include the use of fluorophores and imaging processes to determine the respective arrangements of nucleotides associated with a number of polynucleotides.

In various implementations, calibration regions of a group of polynucleotides can be analyzed to determine a likelihood that one or more errors may occur during a sequencing calibration process. Determining a likelihood that one or more errors may occur during a sequencing calibration process can include determining a number of polynucleotides that have a same nucleotide at one or more positions of their respective calibration regions. In some cases, determining a number of polynucleotides that have a same nucleotide at a particular position of their respective calibration regions can include determining a concentration or percentage of the polynucleotides in the group that have the same nucleotide at the particular position. In particular implementations, the calibration regions of synthesized, physical polynucleotides can be analyzed. In other implementations, polynucleotide data indicating sequences of polynucleotides that have yet to be synthesized can be analyzed. The polynucleotide data can serve as a pattern or template by which the group of polynucleotides can be synthesized.

Determining the number of polynucleotides that have a same nucleotide at one or more positions of their calibration regions can include comparing the nucleotides of the group of polynucleotides to be sequenced at each position of their calibration regions. For example, a number of rounds of comparisons can be performed based on the number of nucleotides in the calibration region. In a first round, the nucleotides in the first position of the calibration regions of the polynucleotides to be sequenced can be compared. In a second round, the nucleotides in the second position of the calibration regions of the polynucleotides to be sequenced can be compared. The rounds of comparison can continue until the nucleotides of the last position of the calibration regions of the polynucleotides to be sequenced are compared.

In particular implementations, various thresholds can be determined to indicate when an error may take place during a sequencing calibration process. For example, a threshold can indicate that if at least a specified number of polynucleotides to be sequenced have the same nucleotide at a position of the calibration region, the likelihood that an error may occur during the sequencing calibration process may be above a threshold percentage. To illustrate, a threshold can indicate that if more than a threshold number, e.g., 10,000, of polynucleotides have the same nucleotide at a position of the calibration region, then the likelihood that an error may occur during calibration is at least 90%. In another illustrative example, a threshold can indicate that if at least a threshold percentage, e.g., 60%, of the polynucleotides to be sequenced have the same nucleotide at a position of the calibration region, then the likelihood that an error may occur during calibration is at least 90%.

In additional implementations, the threshold can correspond to not only a number or percentage of polynucleotides to be sequenced having a same nucleotide at a position of the calibration region, but to a number or percentage of polynucleotides having the same nucleotide at each of a threshold number of positions of the calibration region. That is, a threshold can indicate that when at least 10,000 polynucleotides to be sequenced have the same nucleotide at each of at least four positions of the calibration region, the likelihood that an error may occur during calibration can be above a threshold percentage (e.g., 90%). In some cases, the polynucleotides that make up the threshold number at each position can be different, while in other scenarios the polynucleotides that make up the threshold number at each position can be the same.

In other implementations, the likelihood that an error may occur during a sequencing calibration process can be related to a distribution of each type of nucleotide at one or more positions of the calibration region for a group of polynucleotides to be sequenced. For example, a threshold distribution for each type of nucleotide can be identified and for each position of the calibration region, the number of polynucleotides having each type of nucleotide at that individual position can be determined. In an illustrative example, for a polynucleotide comprised of four types of nucleotides (e.g., A, T, G, C, for DNA or U, A, G, C, for RNA), an expected distribution of each type of nucleotide can be from 20% to 30%. A likelihood that an error may occur during a sequencing calibration process can be based at least partly on whether or not an actual distribution of one or more types of nucleotides at one or more positions of the calibration regions of a group of polynucleotides is outside of the expected distribution. In additional implementations, a likelihood that an error may occur during a sequencing calibration process can be based at least partly on how much an actual distribution of one or more types of nucleotides at one or more positions of the calibration regions of a group of polynucleotides is different from the expected distribution.

In response to determining that the likelihood that an error may occur during a sequencing calibration process is at least a threshold amount for a group of polynucleotides, the calibration regions of the polynucleotides can be modified. The modifications to the calibration regions can decrease the likelihood of one or more errors taking place during a sequencing calibration process. In particular, the nucleotides at one or more positions of the calibration regions of a group of polynucleotides to be sequenced can be changed such that the number of polynucleotides in the group having the same nucleotide at the one or more positions of their calibration regions is less than a threshold number. In this way, the number of positions where at least a specified number of polynucleotides of the group have the same nucleotide is less than a threshold number, and/or the distribution of each nucleotide at individual positions of the calibration regions is within an expected distribution.

In some implementations, calibration regions of a group of polynucleotides can be modified to reduce the likelihood of errors during a sequencing calibration process by adding regions of nucleotides to the polynucleotides being sequenced to replace the original calibration regions. In this way, the nucleotides of the original calibration regions would be shifted in the polynucleotides such that the nucleotides of the newly added calibration regions would be read by the sequencing machine before reading the nucleotides of the original calibration regions. The regions added to the polynucleotides can have sufficient differences at each position to reduce the number of polynucleotides having the same nucleotide at a given position, to reduce the number of positions at which a number of the polynucleotides have the same nucleotide, and/or to provide a distribution of each type of nucleotide at a given position that is within a specified distribution that provides for effective calibration of a sequencing machine.

In another example, the sequence of the nucleotides in the calibration regions of the polynucleotides to be sequenced can be modified by changing the order of the nucleotides in the calibration regions. To illustrate, the nucleotides in the calibration regions of the polynucleotides can be rearranged. In some cases, the order of the nucleotides in the calibration region can be changed according to a random or pseudo-random number generation algorithm. In other situations, the order of the nucleotides can be changed by re-arranging the order of the nucleotides in the calibration region according to a specified scheme. The modified calibration regions with rearranged sequences can have sufficient differences at each position to reduce the number of polynucleotides having the same nucleotide at a given position, to reduce the number of positions at which a number of the polynucleotides have the same nucleotide, and/or to provide a distribution of each type of nucleotide at a given position that is within a specified distribution that provides for effective calibration of a sequencing machine.

In additional implementations, the lengths of the polynucleotides can be varied to provide sufficient differences between nucleotides of their calibration regions to minimize the likelihood that errors may occur during the sequencing calibration process. In some instances, additional nucleotides can be added to the polynucleotides during ligation of the adapters and/or sequencing primer targets during sequencing operations. By adding nucleotides to vary the lengths of the polynucleotides, the calibration regions of the polynucleotides change because the modified calibration regions include one or more of the newly added nucleotides with the remainder of the nucleotides of the modified calibration regions being comprised of nucleotides of the original calibration region. However, since the number of nucleotides added to individual polynucleotides varies, the number of nucleotides of the original calibration regions included in the modified polynucleotides also varies. Thus, the differences at each position of the modified calibration regions can be sufficient to reduce the number of polynucleotides having the same nucleotide at a given position, to reduce the number of positions at which a number of the polynucleotides have the same nucleotide, and/or to provide a distribution of each type of nucleotide at a given position that is within an expected distribution.

Modifying the calibration regions of polynucleotides according to implementations described herein can reduce the likelihood that errors may occur during a sequencing calibration process. In particular, for sequencing machines that utilize sequencing by synthesis processes, the number of polynucleotides having a same nucleotide for a given round of the calibration process is reduced and the ability to distinguish overlap between the illuminated clusters of the polynucleotides being sequenced is increased. Reducing errors during the calibration process according to implementations described herein can make the sequencing process more accurate than failing to account for calibration errors and more efficient than using a lower number of target polynucleotides. In particular, the actual throughput of the sequencing machine can increase because the use of flow cell surface space can be maximized. That is, the surface of the flow cell can be utilized to sequence a greater number of polynucleotides that would have otherwise caused errors to occur during the sequencing process because techniques that rely on decreasing the number of polynucleotides being sequenced or techniques using a number of polynucleotides known to have sufficient differences at individual positions of their calibration regions can be avoided.

FIG. 1 is a schematic diagram of a process 100 to modify calibration regions of polynucleotides. In the illustrative example of FIG. 1, polynucleotides, such as representative polynucleotide 102, can be included in a group of polynucleotides 104. The group of polynucleotides can have a same length in some situations, and differing lengths in other scenarios. The lengths of the polynucleotides included in the group of polynucleotides 104 can represent the number of nucleotides that comprise the individual polynucleotides 102 of the group of polynucleotides 104. In various implementations, the lengths of the group of polynucleotides 104 can be from at least 100 nucleotides to no greater than 600 nucleotides, from at least 125 nucleotides to no greater than 400 nucleotides, from at least 150 nucleotides to no greater than 300 nucleotides, or from at least 175 nucleotides to no greater than 250 nucleotides.

In some cases, the group of polynucleotides can comprise sequences of nucleotides that have already been synthesized. For example, the group of polynucleotides 104 can include naturally occurring polynucleotides, such as genomic DNA. In another example, the group of polynucleotides 104 can include synthetic sequences of nucleotides that have been synthesized. In various implementations, the group of polynucleotides 104 can represent sequences of nucleotides that have yet to be sequenced. In these situations, the group of polynucleotides 104 can include polynucleotide data that represents the sequences of the group of polynucleotides 104. In particular implementations, the group of polynucleotides 104 can encode digital data.

The polynucleotide 102 can include a calibration region 106. The calibration region 106 can include a sequence of nucleotides that is analyzed by a sequencing machine to determine whether or not the sequencing machine is correctly reading sequences of nucleotides. The beginning of a calibration region 106 can include the nucleotide that is closest in proximity to the 5' end of the polynucleotide 102, in some instances. In other situations, the polynucleotide 102 can include an additional calibration region (not shown in FIG. 1) located at the 3' end of the polynucleotide 102 and the beginning of the additional calibration region can include the nucleotide that is closest in proximity to the 3' end of the polynucleotide 102.

In situations where sequencing machines utilized sequencing by synthesis processes, the calibration region 106 can also be read to determine locations on a flow cell of clusters of individual polynucleotides 102. The calibration region 106 can include at least 2 nucleotides, at least 5 nucleotides, at least 8 nucleotides, at least 10 nucleotides, at least 12 nucleotides, at least 15 nucleotides, or at least 18 nucleotides. In addition, the calibration region can include no greater than 35 nucleotides, no greater than 32 nucleotides, no greater than 30 nucleotides, no greater than 28 nucleotides, no greater than 25 nucleotides, no greater than 22 nucleotides, or no greater than 20 nucleotides. In illustrative examples, the calibration region can include from 2 nucleotides to 35 nucleotides, from 5 nucleotides to 30 nucleotides, from 10 nucleotides to 25 nucleotides, from 5 nucleotides to 20 nucleotides, from 7 nucleotides to 15 nucleotides, or from 15 nucleotides to 30 nucleotides.

The size of the calibration region 106 can vary from sequencing machine to sequencing machine. The calibration region 106 can vary by the manufacturer of the sequencing machine. The calibration region 106 can also vary based at least partly on the underlying technology used by a sequencing machine to read sequences of nucleotides. In particular, sequencing machines utilizing some sequencing technologies can utilize a calibration region 106 with more polynucleotides than other sequencing machines using different sequencing technologies.

At 108, the process 100 can include analyzing the calibration regions of the group of polynucleotides 104. Analyzing the calibration regions of the group of polynucleotides 104 can include comparing the nucleotides of the individual polynucleotides 102 at one or more positions of their calibration regions to determine similarities and differences between the nucleotides at the positions of the calibration regions of the group of polynucleotides 104. In illustrative implementations, analyzing the calibration regions of the group of polynucleotides 104 can include comparing the nucleotides in a first position of the calibration regions 106 of the individual polynucleotides 102 of the group of polynucleotides 104 and then comparing the nucleotides in a second position of the calibration regions 106 of the individual polynucleotides 102 of the group of polynucleotides 104. In particular implementations, sequencing alignment techniques can be utilized to determine the sequence identity between calibration regions of polynucleotides. In some cases, a Basic Local Alignment Sequencing Tool (BLAST) technique can be used to determine similarities and differences between nucleotides at one or more positions of the calibration regions of the group of polynucleotides 104.

Analyzing the calibration regions of the group of polynucleotides 104 can include one or more of operations 110, 112, 114. At 110, the process 100 can include determining a number of polynucleotides included in the group of polynucleotides 104 having a same nucleotide in one or more positions of their calibration regions. For example, nucleotides in a position of the calibration regions can be compared to one another and a number of polynucleotides that have the same nucleotide at that position can be determined. To illustrate, the number of polynucleotides that have A in a particular position, such as a first position or a third position, of the calibration region can be determined. In an illustrative example, the number of nucleotides having a same nucleotide at a particular position can be in the hundreds, thousands, or more.

At 112, the process 100 can include determining a number of positions of the calibration regions at which at least a threshold number of the group of polynucleotides 104 have the same nucleotide. The threshold number of polynucleotides can be related to a likelihood that an error may occur during a calibration process due to a same nucleotide being located at one or more positions of a calibration region. In particular, where sequencing machines utilize sequencing by synthesis techniques, the threshold number of polynucleotides can be related to a likelihood of an error occurring during a sequencing machine calibration process due to overclustering. In some situations, the threshold number of polynucleotides can correspond to a concentration of polynucleotides attached to a flow cell of a sequencing machine at which an error may occur due to overclustering during a calibration process of a sequencing machine. In illustrative examples, the threshold number of polynucleotides can indicate a likelihood that an error may occur during a sequencing machine calibration process of 70%, 75%, 80%, 85%, 90%, 95%, 99%, or a likelihood between 70% and 99%.

In some implementations, information obtained from performing operation 110 can be utilized to determine a number of positions of the calibration region at which a threshold number of the group of polynucleotides 104 have the same nucleotide. For example, the numbers of nucleotides at each position of the calibration region that have a same nucleotide can be compared with the threshold number. To illustrate, the results of operation 110 can indicate that a first sub-group of 1000 polynucleotides of the group of polynucleotides 104 have a same nucleotide at a first position of their calibration regions and a second sub-group of 2500 polynucleotides of the group of polynucleotides 104 have a same nucleotide at a fourth position of their calibration regions. In various implementations, a number of consecutive positions of the calibration region can be determined at which at least a threshold number of polynucleotides of the group of polynucleotides 104 have the same nucleotide. In an illustrative example, a first four positions of the respective calibration regions of the group of polynucleotides 104 can have a same nucleotide for at least the threshold number of polynucleotides. In another illustrative example, positions 3-5 of the respective calibration regions of the group of polynucleotides 104 can have a same nucleotide for at least the threshold number of polynucleotides.

At 114, the process 100 can include determining a distribution of each type of nucleotide at each position of the calibration regions of the group of polynucleotides 104. In scenarios where the group of polynucleotides 104 include strands of DNA, a number or percentage of As can be determined at each position of the calibration regions of the group of polynucleotides 104, a number or percentage of Ts can be determined at each position of the calibration regions of the group of polynucleotides 104, a number or percentage of Gs can be determined at each position of the calibration regions of the group of polynucleotides 104, and a number or percentage of Cs can be determined at each position of the calibration regions of the group of polynucleotides 104.

At 116, the process 100 can include determining a likelihood that errors may occur during a sequencing calibration process for the group of polynucleotides 104. In various implementations, the likelihood that errors may occur during a sequencing calibration process can be determined using the results of one or more of operations 110, 112, 114. The operations 110, 112, 114 utilized to determine the likelihood of an error occurring during sequencing calibration can be based on the techniques used to perform sequencing. For example, sequencing machines that implement sequencing by synthesis techniques can utilize at least one of operations 110, 112, 114 to determine the likelihood of an error occurring during sequencing calibration.

In some implementations, a likelihood that errors may occur during a sequencing calibration process can be related to a number of nucleotides having a same nucleotide in one or more positions of the calibration regions of the group of polynucleotides. For example, as the number of polynucleotides having the same nucleotide at one or more positions of their calibration regions increases, the likelihood of an error taking place during a sequencing calibration process can also increase. Additionally, a likelihood that an error may occur during a sequencing calibration process can be based at least partly on a number of positions of the calibration regions at which at least a threshold number of polynucleotides have the same nucleotide. In some cases, the likelihood that an error may occur during a sequencing calibration process can increase as the number of positions at which at least a threshold number of polynucleotides has the same nucleotide increases. Also, the likelihood that an error may occur during a sequencing calibration process can be based at least partly on a number of consecutive positions of the calibration regions at which at least a threshold number of polynucleotides have the same nucleotide. For example, as the number of consecutive positions of the calibration regions at which at least a threshold number of polynucleotides have the same nucleotide increases, the likelihood that an error may occur during a sequencing calibration process can increase.

Further, a likelihood that an error may occur during a sequencing calibration process can be based at least partly on a distribution of each type of nucleotide at each position of the calibration regions of the group of polynucleotides 104. In particular implementations, when the distribution of one or more nucleotides at one or more positions of the calibration regions are outside of a specified distribution that provides for effective calibration of a sequencing machine, the likelihood of an error occurring during a sequencing calibration process can increase. In some instances, a likelihood that an error may occur during a sequencing calibration process can be based at least partly on an amount of difference between an actual distribution of one or more nucleotides at one or more positions of the calibration regions of the group of polynucleotides and a specified distribution of the one or more nucleotides at the one or more positions. That is, as the difference between an actual distribution and specified distribution of one or more nucleotides at one or more positions of the calibration regions increases, the likelihood that an error may occur during the sequencing calibration process can increase. Also, the number of nucleotides having a distribution outside of a specified distribution can affect the likelihood that an error may occur during a sequencing calibration process. In addition, the number of positions at which the distribution of one or more nucleotides is different from a specified distribution can also affect the likelihood that an error may occur during a sequencing calibration process.

In situations where the likelihood that an error may occur during a sequencing calibration process is at least a threshold likelihood, the process 100 at 118 can include modifying the sequence of nucleotides in the calibration regions of at least a portion of the group of polynucleotides 104. Modifying calibration regions can decrease the likelihood that an error may occur during a sequencing calibration process. In some cases, modifying at least a portion of the calibration regions of at least a portion of the group of the group of polynucleotides 104 can decrease the likelihood that an error may occur during a sequencing calibration process. In particular, the likelihood that an error may occur during a sequencing calibration process can decrease below a threshold likelihood in response to the modifications to the calibration regions of at least a portion of the group of polynucleotides 104. In various implementations, modifying the calibration regions of at least a portion of the group of polynucleotides 104 can decrease a number of the group of polynucleotides 104 that have a same nucleotide at one or more positions of their calibration regions. Additionally, in some instances, modifying the calibration regions of at least a portion of the group of polynucleotides 104 can decrease a number of positions of the calibration regions of the group of polynucleotides 104 at which at least a threshold number of the group of polynucleotides 104 have the same nucleotide. Further, modifying the calibration regions of at least a portion of the group of polynucleotides 104 can decrease a number of positions of the calibration regions that have a distribution of one or more nucleotides outside of a specified distribution.

Modifying the sequence of nucleotides in the calibration regions of at least a portion of the group of polynucleotides 104 can include adding new calibration regions that a sequencing machine would read before reading the original calibration regions, such that a sequencing machine reads the nucleotides of the new calibration region during the calibration process rather than reading the nucleotides of the original calibration region. In some implementations, the new calibration regions can include a distribution of nucleotides that more closely corresponds to a distribution of nucleotides expected by the sequencing machine. For example, the distribution of nucleotides in the new calibration regions can include from 15-35% of each type of nucleotide that comprises the group of polynucleotides 104. To illustrate, in situations where the group of polynucleotides 104 comprise strands of DNA, the new calibration regions can include from about 15% to about 35% A, from about 15% to about 35% T, from about 15% to about 35% G, and from about 15% to about 35% C. In other examples, the new calibration regions can include from about 20% to about 30% A, from about 20% to about 30% T, from about 20% to about 30% G, and from about 20% to about 30% C. In the cases where the group of polynucleotides 104 comprise strands of RNA, the new calibration regions can include from about 15% to about 35% A, from about 15% to about 35% T, from about 15% to about 35% G, and from about 15% to about 35% C. In additional examples, the new calibration regions can include from about 20% to about 30% U, from about 20% to about 30% T, from about 20% to about 30% G, and from about 20% to about 30% C. In addition, the new calibration regions can be designed such that a number of polynucleotides included in the group of polynucleotides 104 having a same nucleotide in any given position is less than a threshold number.

Modifying the sequence of nucleotides in the calibration regions of at least a portion of the group of polynucleotides 104 can also include modifying the arrangement of nucleotides in the calibration regions of at least a portion of the group of polynucleotides 104. In some implementations, the order of the nucleotides in the calibration regions can be modified. The order of the nucleotides included in the calibration regions can be modified such that the number of polynucleotides of the group of polynucleotides 104 having the same nucleotide at a given position is less than a threshold number and/or such that the distribution of nucleotides at any given position of the calibration regions is within an expected distribution. In some cases, the modified order of the nucleotides included in the calibration regions of at least a portion of the group of polynucleotides 104 can be determined based on a pseudo-random number generation algorithm. In other cases, the modified order of the nucleotides included in the calibration regions of at least a portion of the group of polynucleotides 104 can be based on a particular scheme. For example, the modified order of the nucleotides included in the calibration regions of at least a portion of the group of polynucleotides 104 can be based on a rotation where a last nucleotide of a first polynucleotide replaces the first nucleotide of a second polynucleotide with the remainder of the nucleotides shifting positions. To illustrate, a calibration region of a first polynucleotide of AGCCTGGAT can be modified to be GAGCCTGGA for the second polynucleotide.

In situations where the order of the nucleotides included in the calibration regions of at least a portion of the polynucleotides 104 is modified, the modifications to the order can be tracked. In some instances, the modifications to the order of the nucleotides included in the calibration regions of at least a portion of the group of polynucleotides 104 can be reversible such that the original order of the nucleotides in the calibration regions can be reproduced from the modified order. In various implementations, a hash code or a key utilized to modify the order of the nucleotides in the calibration regions of at least a portion of the group of polynucleotides 104 can be used to reproduce the original sequence of nucleotides of the calibration regions. Additionally, the changes to the order of the nucleotides of the calibration regions can be tracked in a data structure, such as in a look-up table, and the data structure can be used to reproduce the original order of nucleotides of the calibration regions.

Further, modifying the sequence of nucleotides in the calibration regions of at least a portion of the group of polynucleotides 104 can include modifying the lengths of polynucleotides included in the group of polynucleotides 104. The lengths of the polynucleotides can be modified by adding a number of nucleotides to the calibrations regions of polynucleotides included in the group of polynucleotides 104. The lengths of the polynucleotides can be modified by adding sequences of varying length to the calibration regions. For example, a first number of polynucleotides of the group of polynucleotides 104 can have sequences including 5 nucleotides added to their respective calibration regions, while a second number of polynucleotides of the group of polynucleotides 104 can have sequences including 8 nucleotides added to their respective calibration regions. Additionally, the nucleotides added to the calibration regions can have varying sequences. To illustrate, the nucleotides and the order of the nucleotides included in the sequences added to polynucleotides of the group of polynucleotides 104 can vary. In an illustrative example, a first sequence of AGCC can be added to a calibration region of a first polynucleotide, a second sequence of GCTTAC can be added to a calibration region of a second polynucleotide, and a third sequence of TCCGGTAAG can be added to a calibration region of a third polynucleotide. By producing polynucleotides of varying lengths, the calibration regions of polynucleotides can also change. In this way, sequence of nucleotides is read by the sequencing machine during the calibration process that is different from the original sequences of the calibration regions. Accordingly, differences between the calibration regions of the group of polynucleotides 104 can be sufficient to minimize or eliminate the errors produced during a sequencing calibration process.

The process 100 also includes sequencing preparation at 120. Sequencing preparation can include adding sequences to polynucleotides before the sequencing operation takes place. In some implementations, sequences can be added to polynucleotides using an enzyme, such as a ligase. In particular implementations, a DNA ligase can be used to add sequences to the polynucleotides. The sequences added to the polynucleotides can include adapters that couple the polynucleotides to a flow cell during the sequencing process. Additionally, the sequences added to the polynucleotides can include sequencing primer targets that can be used in the replication and amplification the polynucleotides during the sequencing process. In some cases, the modifications to the calibration regions of the group of polynucleotides 104 can take place before sequencing preparation at 120. For example, the order of the nucleotides included in the calibration regions of at least a portion of the group of polynucleotides 104 can be modified before the sequencing preparation at 120. Additionally, a new calibration region can be added to at least a portion of the group of polynucleotides 104 before the sequencing preparation at 120. In other cases, the modifications to the calibration regions of polynucleotides included in the group of polynucleotides 104 can take place during the sequencing preparation at 120. To illustrate, sequences of varying length can be added to polynucleotides included in the group of polynucleotides 104 during the sequencing preparation at 120. In an illustrative example, as the adapters and/or sequencing primer targets are added to polynucleotides of the group of polynucleotides 104, an additional sequence can be added to the calibration regions of the polynucleotides to produce polynucleotides of varying length.

At 122, the process 100 can include calibration of the sequencing machine used to read the sequences of the group of polynucleotides 104. Calibration of the sequencing machine can include reading each nucleotide included in the calibration regions of the group of polynucleotides 104. In situations where the sequencing machine utilizes sequencing by synthesis techniques, for each position in the calibration regions, the sequencing machine can add fluorophore bound nucleotides that couple with complementary nucleotides in the calibration regions of the group of polynucleotides 104 and excite the fluorophores using electromagnetic radiation. The operations that take place with respect to 108, 110, 112, 114, 116, 118 are intended to minimize any errors that may occur during calibration at 122 due to the same nucleotide being located at one or more positions of at least a threshold number of the group of polynucleotides 104. In some implementations, the operations that take place with respect to 108, 110, 112, 114, 116, 118 are intended to minimize any errors that may occur during calibration at 122 due to overclustering.

At 124, the process 100 can include sequence reading. Sequence reading can include determining a type of nucleotide at each position of the sequences of the group of polynucleotides 104. The sequence reading performed at 124 can produce sequence data 126. The sequence data can include the sequences of nucleotides that comprise each of the group of polynucleotides 104 that have been read.

Figure 2:
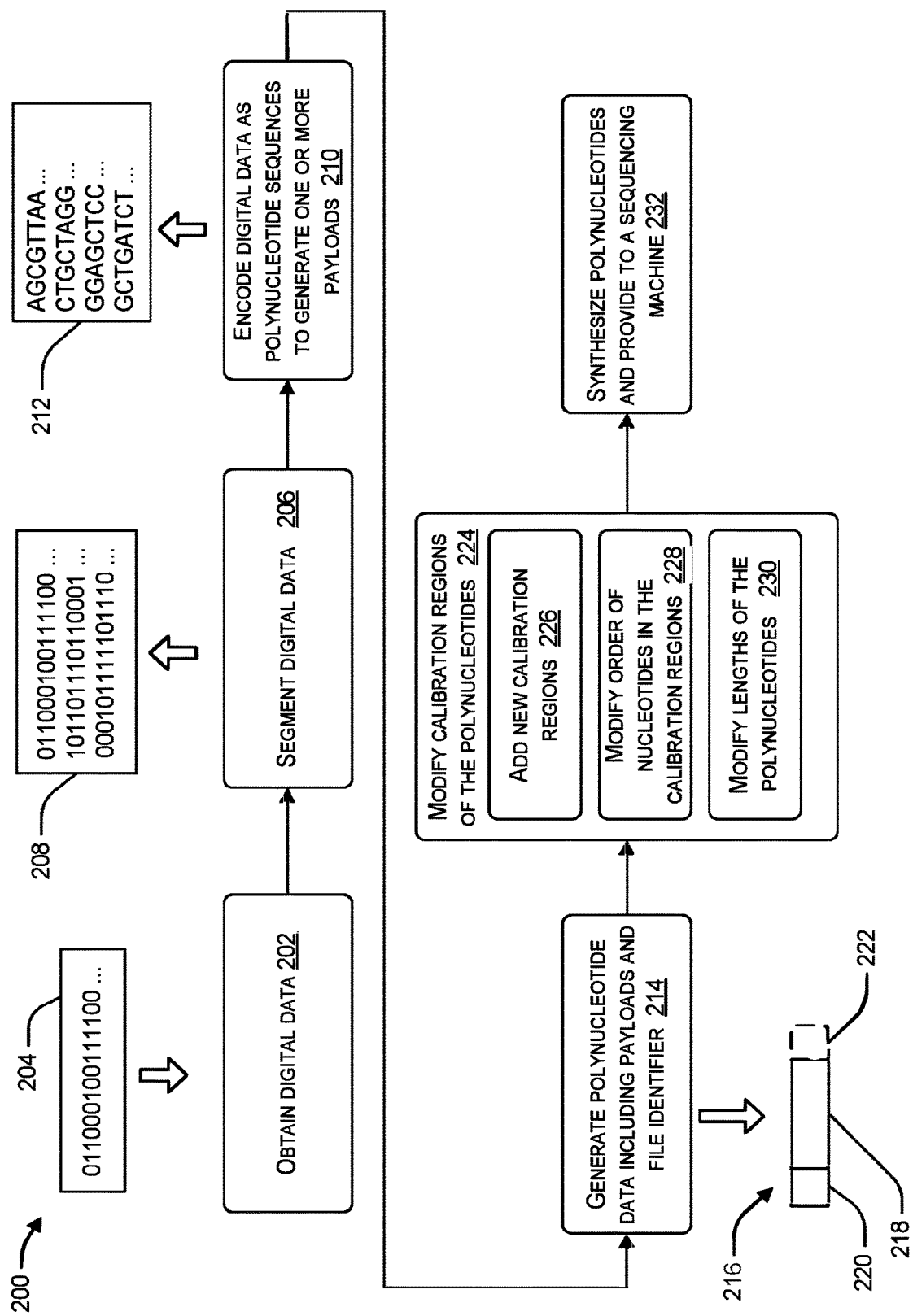
FIG. 2 shows a schematic representation of an example process to modify calibration regions of polynucleotides that encode digital data.

FIG. 2 shows a schematic diagram of a process 200 to design polynucleotides having sequences that minimize errors during the calibration of sequencing machines. At 202, the process 200 can include obtaining digital data 204. The digital data 204 can include a sequence of 1s and 0s that can be processed by a computing device. The digital data 204 can include input and/or output related to one or more applications. In illustrative implementations, the digital data 204 can be related to at least one of audio content, video content, image content, or text content.

At 206, the process 200 can include segmenting the digital data 204. In some scenarios, the length of the string of bits of the digital data 204 can be segmented into a group of bit strings 208. The digital data 204 may be segmented because the length of polynucleotides encoding digital data can be limited due to polynucleotides beyond a threshold length producing errors during polynucleotide replication and amplification processes. In these situations, the bit string encoding the digital data 204 can be divided into segments of bits that can be encoded with sequences of nucleotides having a length that is no greater than the threshold length.

At 210, the process 200 can include encoding the group of bit strings 208 as sequences of nucleotides. The individual sequences of nucleotides that encode the group of bit strings 208 are referred to herein as "payloads." Thus, the encoding of the bit strings 208 as sequences of nucleotides generates a group of payloads 212. The encoding of the group of bit strings 208 as the group of payloads 212 can be performed according to one or more techniques that associate one or more bits with one or more nucleotides. In some implementations, a first group of bits can be associated with a first nucleotide, a second group of bits can be associated with a second nucleotide, a third group of bits can be associated with a third nucleotide, and a fourth group of bits can be associated with a fourth nucleotide. In an illustrative example, a bit pair 00 can correspond to a first nucleotide, such as A; a second bit pair 01 can correspond to a second nucleotide, such as C; a third bit pair 10 can correspond to a third nucleotide, such as G; and a fourth bit pair 11 can correspond to a fourth nucleotide, such as T. In another illustrative example, the digital data 204 can be mapped to a base-4 string with each number in base 4 mapping to a corresponding letter representing a nucleotide. To illustrate, 0, 1, 2, and 3 can each map to one of A, C, G, or T. In an additional illustrative example, the bits of the group of bit strings 208 can be mapped to a base-3 string with a nucleotide mapping to each number of the base 3 string (e.g., 0, 1, 2) based on a rotating code.

At 214, the process 200 includes generating polynucleotide data that corresponds to polynucleotides including the group of payloads 212 and one or more file identifiers. File identifiers can be used to reassemble the group of bit strings 208 back into the digital data 204 after decoding of the group of payloads 212. In particular, file identifiers can correspond to the original digital data 204 that is being encoded by the group of payloads 212. In some examples, file identifiers can individually be sequences of nucleotides that are the same for a particular file. To illustrate, the digital data 204 can be associated with a file identifier and each payload of the group of payloads 212 can be associated with the file identifier of the digital data 204. In the illustrative example of FIG. 2, a representative polynucleotide 216 encoding at least a portion of the digital data 204 can be produced that includes a payload 218 from the group of payloads 212 and a file identifier 220 that corresponds to the digital data 204. In some implementations, the polynucleotide 216 can also include an additional file identifier 222 that also corresponds to the digital data 204. In some cases, the file identifier 220 and the additional file identifier 222 can include a same sequence of nucleotides. In other situations, the file identifier 220 and the additional file identifier 222 can include different sequences of nucleotides. In instances where the file identifier 220 and the additional file identifier 222 include different sequences of nucleotides, both the file identifier 220 and the additional file identifier 222 can correspond to the digital data 204. In various implementations, a data structure can store information indicating the one or more file identifiers associated with each digital file. For example, a data structure, such as a lookup table, can store information indicating one or more file identifiers associated with the digital data 204.

Additionally, the polynucleotide 216 can include nucleotides that represent information in addition to the file identifier 220. For example, the polynucleotide 216 can include one or more nucleotides that indicate ordering information. The ordering information can indicate a location within the digital data 204 for each bit string of the group of bit strings 208 encoded by the group of payloads 212. Thus, in some implementations, file identifiers and ordering information can be used to reproduce the original bit string of the digital data 204 from the polynucleotides related to the polynucleotide data generated at 214.

At 224, a calibration region of the polynucleotides can be modified. The modification of the calibration regions of polynucleotides can be performed by modifying the polynucleotide data associated with each of the polynucleotides. The calibration regions can be modified in situations where a likelihood that an error may occur during a sequencing calibration process is above a threshold likelihood. In some cases, the calibration regions can comprise a number of nucleotides of the file identifier(s) of the polynucleotides. In a particular example, a calibration region of the polynucleotide 216 can include a number of nucleotides of the file identifier 220 when sequencing begins from the 5' end of the polynucleotide 216. In another example, a calibration region of the polynucleotide 216 can include a number of nucleotides of the additional file identifier 222 when sequencing begins from the 3' end of the polynucleotide 216. In various implementations, the calibration regions can also include one or more nucleotides of the payloads of the polynucleotides. To illustrate, when a file identifier of a polynucleotide has fewer nucleotides than the calibration region, one or more nucleotides of the payload can comprise a remainder of the calibration region.

Modifying the calibration region of polynucleotides at 224 can include adding a new calibration region at 226. New calibration regions can be added to polynucleotides by coupling additional sequences of nucleotides to the polynucleotides. In some cases, data for a group of new calibration regions can be generated for a group of polynucleotides and the sequences of nucleotides included in the group of new calibration regions can be tested to determine a likelihood that an error may occur during a sequencing calibration process for the new calibration regions. The new calibration regions can include individual sequences of nucleotides that have less than a threshold number of positions where at least a threshold number of the polynucleotides have a same nucleotide. In the illustrative example of FIG. 2, adding a calibration region to the polynucleotide 216 can include adding a sequence of nucleotides before the file identifier 220 and/or before the additional file identifier 222. Accordingly, during the calibration process, a sequencing machine reads the new calibration region added to the polynucleotide 216 instead of reading the file identifier 220 or the additional file identifier 222.

In addition, modifying a calibration region of the polynucleotides can include, at 228, modifying the order of nucleotides in the calibration regions of the polynucleotides. Modifying the order of the nucleotides in the calibration regions can include replacing the nucleotides at each position of the calibration regions with other nucleotides. For example, modifying the calibration regions of the polynucleotide 216 can include replacing a first nucleotide at a first position of the calibration region with a second nucleotide from a second position of the calibration region. In this way, each position of a calibration region can be substituted by a nucleotide from another position of the calibration region. Thus, the number of each type of nucleotide (e.g., A, T, G, C) within the calibration region can remain the same, but the ordering of the nucleotides in the calibration region is different. In some implementations, the sequence of nucleotides in calibration regions can be modified by randomizing the order of the nucleotides according to a pseudo-random number generation algorithm. In other implementations, the sequence of nucleotides in the calibration regions can be arranged according to a specified scheme that changes the order of the nucleotides in the calibration regions.

Further, modifying calibration regions of polynucleotides can include, at 230, modifying the lengths of the polynucleotides. Modifying the lengths of the polynucleotides can include adding sequences of varying length to individual polynucleotides. For example, sequences added to the polynucleotides can have from 3 to 15 nucleotides, from 4 to 12 nucleotides, from 5 to 10 nucleotides, from 8 to 15 nucleotides, or from 4 to 8 nucleotides. To illustrate, a first sequence of nucleotides added to the polynucleotides can have a first length, such as 6 nucleotides, and a second sequence of nucleotides added to the polynucleotides can have a second length, such as 9 nucleotides. The sequences added to the polynucleotides can also have varying nucleotides at each position, in some cases.

The sequences added to the polynucleotides can be tracked in order to separately identify the file identifiers and the payloads from the sequences that have been added. In this way, an analysis of the reads of the polynucleotides read by a sequencing machine can identify the sequence added to the polynucleotide, the file identifier, and the payload because the sequence of nucleotides for each of component of the polynucleotide is known. In some cases, the sequences added to the polynucleotides can have less than a threshold number of positions that include a same nucleotide.

After modifying the calibration regions, at 232, the polynucleotide data can be used to synthesize the corresponding polynucleotides and the polynucleotides can be provided to a sequencing machine. The sequencing machine can read the polynucleotides and provide the sequence of nucleotides that corresponds with each individual polynucleotide being sequenced. In some cases, the polynucleotides can be sequenced as part of a data retrieval process. For example, in response to receiving a request for the digital data 204, polynucleotides including the group of payloads 212 that encode the digital data 204 can be sequenced. After sequencing the polynucleotides that include the group of payloads 212, the group of payloads 212 can be extracted from the polynucleotides, decoded, and ordered to reproduce the digital data 204. The digital data 204 can then be processed by a computing device.

Figure 3:
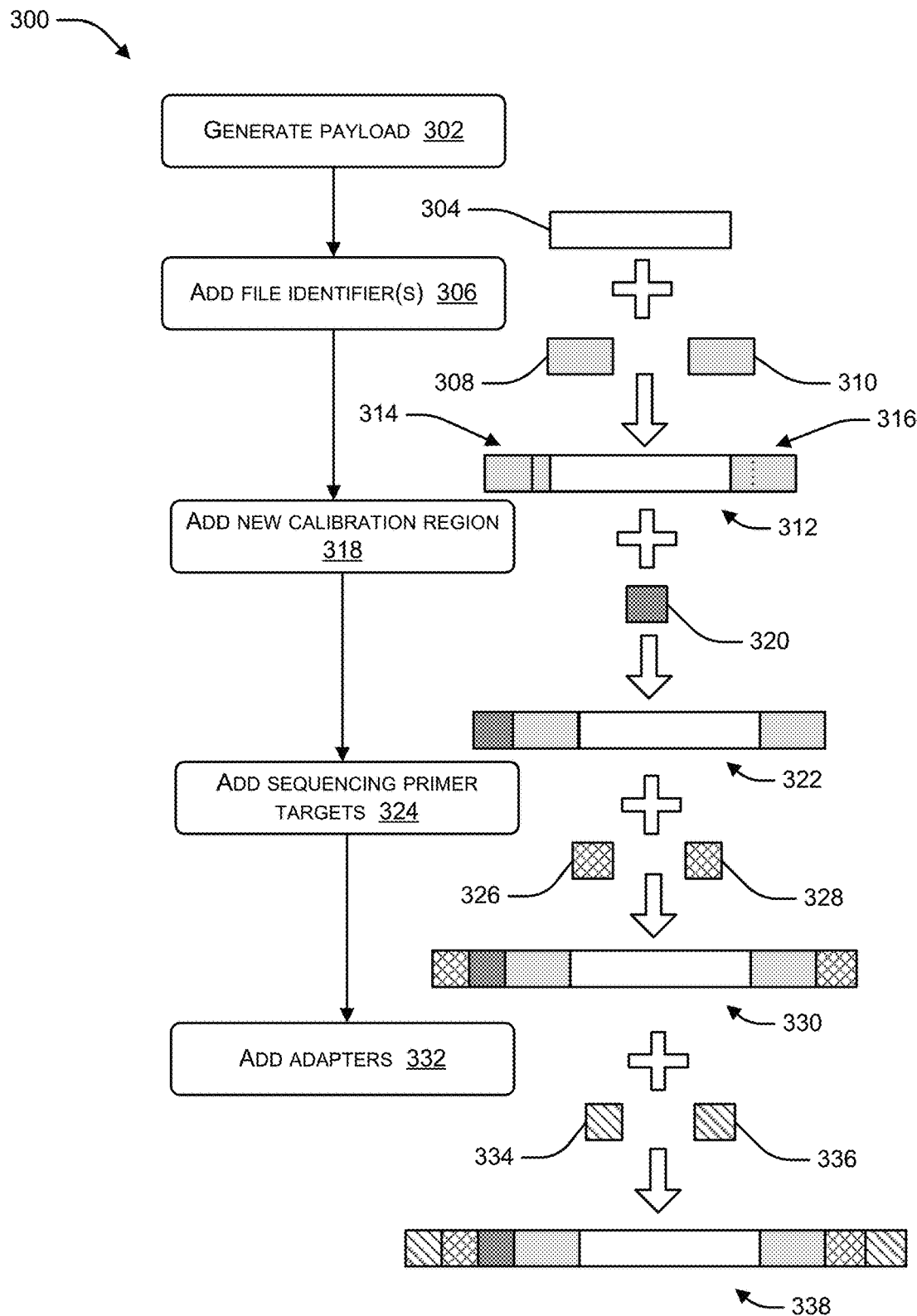
FIG. 3 shows a flow diagram of an example process to modify calibration regions of polynucleotides by adding a new calibration region to the polynucleotides.

FIG. 3 is a schematic diagram of a process 300 to modify a calibration region of a polynucleotide by adding a new calibration region to the polynucleotide. In some cases, modifying a calibration region of a polynucleotide can include modifying data that corresponds to the polynucleotide. At 302, the process 300 can include generating data that corresponds to a payload 304. The payload 304 can include a sequence of nucleotides that encodes digital data. The payload 304 can be generated by a computing device using an encoding scheme that correlates bits of the digital data with nucleotides. In some implementations, the payload 304 can be synthesized after data corresponding to the payload 304 is generated by the computing device.

At 306, the process 300 can include adding one or more file identifiers to the payload 304. In the illustrative example of FIG. 3, two file identifiers are added to the payload 304, a first file identifier 308 and a second file identifier 310, to produce a first sequence of nucleotides 312. In some cases, the first file identifier 308 and the second file identifier 310 can include a same sequence of nucleotides. In other situations, the first file identifier 308 and the second file identifier 310 can include different sequences of nucleotides. In various implementations, data corresponding to the file identifiers 308 and 310 can be generated and data corresponding to the first sequence of nucleotides 312 can be generated by a computing device before synthesizing the first sequence of nucleotides 312.

Additionally, in some implementations, at least a portion of the first file identifier 308 and/or the second file identifier 310 can include primer targets. That is, at least a portion of the first file identifier 308 and/or the second file identifier 310 can include sequences of nucleotides that primers can couple with during polynucleotide replication and amplification operations, such as during one or more PCR processes. The primers related to the first file identifier 308 and/or the second file identifier 310 can be utilized in PCR processes that are not performed during the sequencing of the polynucleotides. For example, primers related to the first file identifier 308 and/or the second file identifier 310 can be utilized during the retrieval of polynucleotides corresponding to digital data before sequencing takes place.

In particular implementations, the first file identifier 308 and/or the second file identifier 310 can have the same nucleotide at one or more positions with file identifiers of other payloads that may be sequenced with the payload 304. The number of positions of the file identifiers and/or the number of polynucleotides including the file identifiers having the same nucleotide at one or more positions as the first file identifier 308 and/or the second file identifier 310 can be at least a threshold number of positions and/or at least a threshold number of polynucleotides. The threshold number of positions and/or the threshold number of polynucleotides can correspond to a particular likelihood of errors occurring during a sequencing calibration process. In some examples, the first file identifier 308 and/or the second file identifier 310 can be the same as file identifiers included in other polynucleotides that may be sequenced with a polynucleotide including the first sequence of nucleotides 312.

The first sequence of nucleotides 312 can include a first calibration region 314 that can comprise at least a portion of the nucleotides of the first file identifier 308. Additionally, or alternatively, the first sequence of nucleotides 312 can include a second calibration region 316 that can comprise at least a portion of the nucleotides of the second file identifier 310. The first calibration region 314 and/or the second calibration region 316 can correspond to a number of nucleotides used by a sequencing machine during a calibration process for the sequencing machine. In some cases, the first calibration region 314 and the second calibration region 316 can include a same number of nucleotides. Additionally, the number of nucleotides included in the first calibration region 314 and/or the second calibration region 316 can be based at least partly on a manufacturer of the sequencing machine, a sequencing technology utilized by the sequencing machine, or both.

At 318, the process 300 can include adding a new calibration region 320 to the first sequence of nucleotides 312 to produce a second sequence of nucleotides 322. The new calibration region 320 can have fewer positions with a same nucleotide as other polynucleotides to be sequenced with the second polynucleotide. Additionally, fewer polynucleotides to be sequenced with the second sequence of nucleotides 322 can have calibration regions that include a same nucleotide as one or more positions of the calibration region 314 and/or the additional calibration region 316. The number of polynucleotides included in the new calibration region 320 can be the same as the number of nucleotides of the first calibration region 314. In additional implementations, the number of nucleotides included in the new calibration region 320 can be different from the number of polynucleotides of the first calibration region 314. Data corresponding to the new calibration region 320 can be generated and data corresponding to the second sequence of nucleotides 322 can be generated by a computing device before synthesizing the second sequence of nucleotides 322.

At 324, the process 300 can include adding sequencing primer targets to the second sequence of nucleotides 322, such as a first sequencing primer target 326 and a second sequencing primer target 328, to produce a third sequence of nucleotides 330. The first sequencing primer target 326 and the second sequencing primer target 328 can include sequences of nucleotides used to replicate and amplify polynucleotides during a sequencing process. In particular, the first sequencing primer target 326 and the second sequencing primer target 328 can include sequences of nucleotides that are complementary to sequencing primers used to amplify and replicate polynucleotides. The sequencing primers can bind to the first sequencing primer target 326 and/or the second sequencing primer target 328 to add complementary nucleotides to the second sequence of nucleotides 322.

In some cases, the first sequencing primer target 326 and the second sequencing primer target 328 can include a same sequence of nucleotides, while in other situations, the first sequencing primer target 326 and the second sequencing primer target 328 can include different sequences of nucleotides. In various implementations, the first sequencing primer target 326 and the second sequencing primer target 328 can include sequences of nucleotides that are different from the payload 304, the first file identifier 308, the second file identifier 310, and/or the new calibration region 320. The third sequence of nucleotides 330 can be synthesized during the sequencing process.

At 332, the process 300 can include adding adapters to the third sequence of nucleotides 330, such as a first adapter 334 and a second adapter 336, to produce a fourth sequence of nucleotides 338. The first adapter 334 and the second adapter 336 can include sequences of nucleotides to attach the fourth sequence of nucleotides 338 to a surface of a sequencing machine, such as a surface of a flow cell, during the sequencing process. In some cases, the first adapter 334 and the second adapter 336 can include a same sequence of nucleotides, while in other situations, the first adapter 334 and the second adapter 336 can include different sequences of nucleotides. In various implementations, the first adapter 334 and the second adapter 336 can include sequences of nucleotides that are different from the payload 304, the first file identifier 308, the second file identifier 310, the new calibration region 320, the first sequencing primer target 326, and the second sequencing primer target 328. The fourth sequence of nucleotides 338 can be synthesized during the sequencing process.

Although the illustrative example of FIG. 3 shows sequences of nucleotides 312, 322, 330, 338 having a number of components, the sequences of nucleotides 312, 322, 330, 338 can include additional components. For example, the sequences of nucleotides 312, 322, 330, 338 can include one or more regions of nucleotides that correspond to location information that indicates a location of bits encoded by a respective payload within a larger string of bits. In another example, the sequences of nucleotides 312, 322, 330, 338 can include one or more regions of nucleotides that correspond to error correction information that can be used to correct errors that may occur during polynucleotide replication and amplification operations that take place during the retrieval of digital data encoded by polynucleotides. In addition, although the illustrative example of FIG. 3 has been described with respect to adding a new calibration region to the first calibration region 314, a new calibration can additionally, or alternatively, be added to the second calibration region 316.

Figure 4:
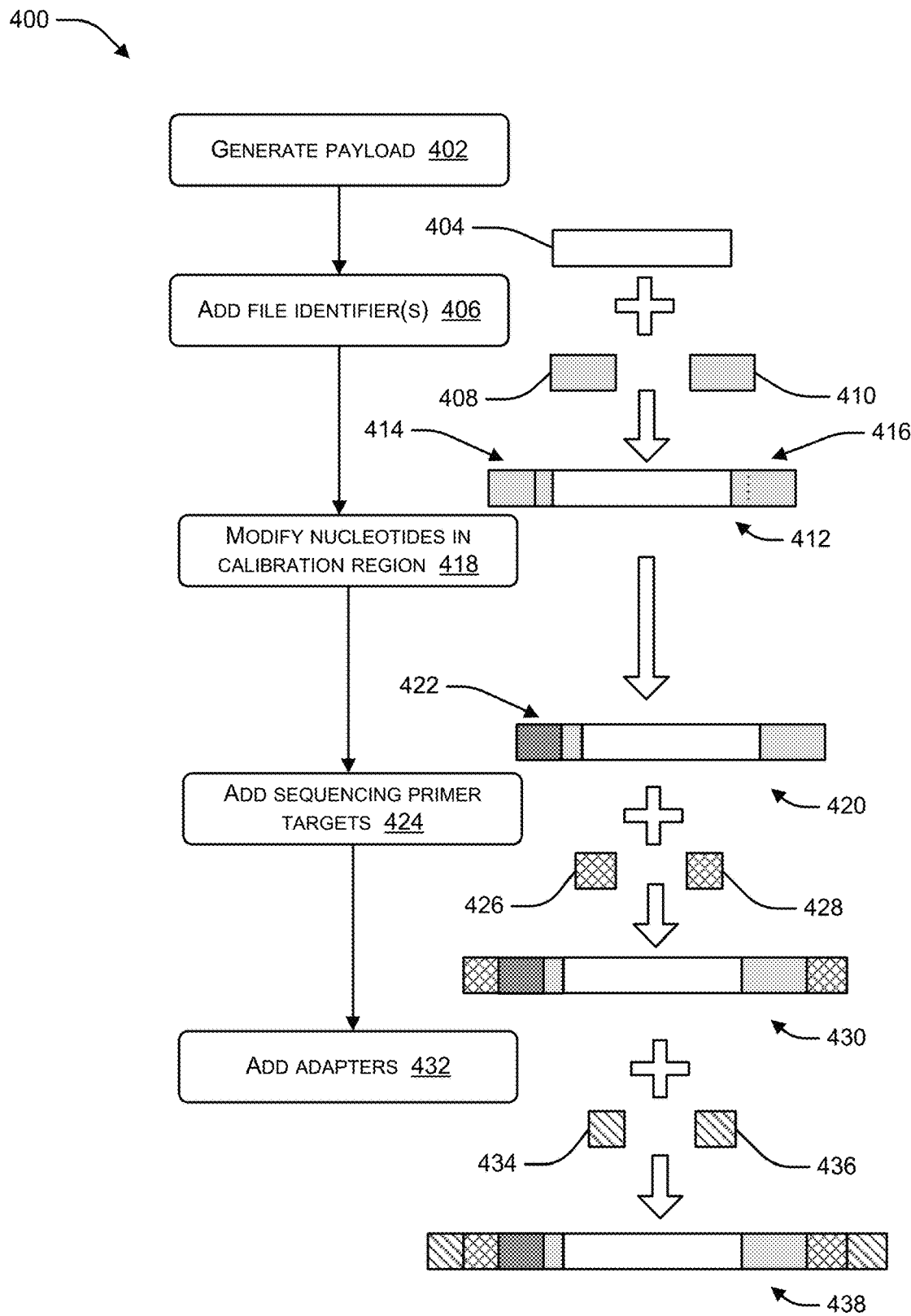
FIG. 4 shows a flow diagram of an example process to modify calibration regions of polynucleotides by modifying the arrangement of nucleotides in the calibration regions.

FIG. 4 is a schematic diagram of a process 400 to modify a calibration region of a polynucleotide by modifying the arrangement of nucleotides in the calibration region of the polynucleotide. At 402, the process 400 can include generating a payload 404. The payload 404 can include a sequence of nucleotides that encodes digital data. Data corresponding to the payload 404 can be generated by a computing device using an encoding scheme that correlates bits of the digital data with nucleotides. In some implementations, the payload 404 can be synthesized after the data corresponding to the payload 404 is generated by the computing device.

At 406, the process 400 can include adding one or more file identifiers to the payload 404. In the illustrative example of FIG. 4, two file identifiers are added to the payload 404, a first file identifier 408 and a second file identifier 410, to produce a first sequence of nucleotides 412. In some cases, the first file identifier 408 and the second file identifier 410 can include a same sequence of nucleotides. In other situations, the first file identifier 408 and the second file identifier 410 can include different sequences of nucleotides. In various implementations, data corresponding to the file identifiers 408 and 410 can be generated and data corresponding to the first sequence of nucleotides 412 can be generated by a computing device before synthesizing the first sequence of nucleotides 412.

In particular implementations, the first file identifier 408 and/or the second file identifier 410 can have the same nucleotide at one or more positions with file identifiers of other payloads that may be sequenced with the payload 404. The number of positions of the file identifiers and/or the number of polynucleotides including the file identifiers having the same nucleotide at one or more positions as the first file identifier 408 and/or the second file identifier 410 can be at least a threshold number of positions and/or at least a threshold number of polynucleotides. The threshold number of positions and/or the threshold number of polynucleotides can correspond to a particular likelihood of errors occurring during a sequencing calibration process.

Additionally, in some implementations, at least a portion of the first file identifier 408 and/or the second file identifier 410 can include primer targets. That is, at least a portion of the first file identifier 408 and/or the second file identifier 410 can include sequences of nucleotides that primers can couple with during polynucleotide replication and amplification operations, such as during one or more PCR processes. The primers related to the first file identifier 408 and/or the second file identifier 410 can be utilized in PCR processes that are not performed during the sequencing of the polynucleotides. For example, primers related to the first file identifier 408 and/or the second file identifier 410 can be utilized during the retrieval of polynucleotides corresponding to digital data before sequencing takes place.

The first sequence of polynucleotides 412 can include a first calibration region 414 that can comprise at least a portion of the nucleotides of the first file identifier 408. Additionally, or alternatively, the first sequence of polynucleotides 412 can include a second calibration region 416 that can comprise at least a portion of the nucleotides of the second file identifier 410. The first calibration region 414 and/or the second calibration region 416 can correspond to a number of nucleotides used by a sequencing machine during a calibration process for the sequencing machine. In some cases, the first calibration region 414 and the second calibration region 416 can include a same number of nucleotides. Additionally, the number of nucleotides included in the first calibration region 414 and/or the second calibration region 416 can be based at least partly on a manufacturer of the sequencing machine, a sequencing technology utilized by the sequencing machine, or both.

At 418, the process 400 can include modifying nucleotides of the first calibration region 414 to produce a second sequence of nucleotides 420 including a modified calibration region 422. Modifying the nucleotides of the first calibration region 414 can include changing the order of nucleotides included in the first calibration region 414. That is, the amount of each type of nucleotide (e.g., A, T, G, C for DNA or T, U, G, C for RNA) of the first calibration region 414 can remain the same, but the arrangement of the nucleotides within the modified calibration region 422 can be different from the arrangement of nucleotides within the first calibration region 414. Data corresponding to the first calibration region 414 can be modified to produce additional data corresponding to the modified calibration region 422 by a computing device before the synthesis of the second sequence of nucleotides 420.

In some cases, the nucleotides of the modified calibration region 422 can be arranged according to a specified scheme. For example, the sequence of nucleotides of the first calibration region 414 can be shifted by at least one nucleotide at each position. To illustrate, a first nucleotide of the first calibration region 414 can be shifted to the second position of the modified calibration region 422 and a second nucleotide of the first calibration region 414 can be shifted to a third position of the modified calibration region 422. The shifting of the nucleotides of the first calibration region 414 can continue until the second to the last nucleotide of the first calibration region 414 becomes the last nucleotide of the modified calibration region 422 and the last nucleotide of the first calibration region 414 becomes the first nucleotide of the modified calibration region 422. In another example, the nucleotides of the first calibration region 414 can be shifted by two positions to produce the modified calibration region 422. In this example, the first nucleotide of the first calibration region 414 can become the third nucleotide of the modified calibration region 422 and the second nucleotide of the first calibration region 414 can become the fourth nucleotide of the modified calibration region 422. Continuing with this example, the third to last nucleotide of the first calibration region 414 can become the last nucleotide of the modified calibration region 422 while the second to last nucleotide and the last nucleotide of the first calibration region 414 can become the first nucleotide and the second nucleotide, respectively, of the modified calibration region 422.

Additionally, the arrangement of nucleotides of the first calibration region 414 can be modified according to a pseudorandom number generation algorithm to produce the modified calibration region 422. In particular implementations, the nucleotides included in the first calibration region 414 can be represented numerically according to a scheme and combined with a hash code or a key. The resulting output can then be used to generate a new sequence of nucleotides according to the scheme. The new sequence of nucleotides can comprise the modified calibration region 422.

Further, the changes made to produce the modified calibration region 422 from the first calibration region 414 can be monitored and tracked. By monitoring and tracking the changes between the first calibration region 414 and the modified calibration region 422, the sequence of nucleotides of the first calibration region 414 can be reproduced from the modified calibration region 422. In some cases, the sequence of nucleotides of the first calibration region 414 may be reproduced from the modified calibration region 422 during decoding of the payload 404 and the first file identifier 408 to determine the digital data encoded by the payload 404 and to determine the file that the payload 404 is associated with. In an illustrative example, the sequence of nucleotides of the modified calibration region 422 can be stored in a data structure in association with the sequence of nucleotides of the first calibration region 414. In these situations, when the sequence of nucleotides of the modified calibration region 422 is detected during decoding, the data structure can be used to determine that the modified calibration region 422 corresponds to the first calibration region 414 and the sequence of nucleotides of the first calibration region 414 can then be analyzed to reassemble the first file identifier 408 and determine the digital data file that includes bits encoded by the payload 404.

At 424, the process 400 can include adding sequencing primer targets to the second sequence of nucleotides 420, such as a first sequencing primer target 426 and a second sequencing primer target 428, to produce a third sequence of nucleotides 430. The first sequencing primer target 426 and the second sequencing primer target 428 can include sequences of nucleotides used to replicate and amplify polynucleotides during a sequencing process. The first sequencing primer target 426 and the second sequencing primer target 428 can include sequences of nucleotides used to replicate and amplify polynucleotides during a sequencing process. In particular, the first sequencing primer target 426 and the second sequencing primer target 428 can include sequences of nucleotides that are complementary to sequencing primers used to amplify and replicate polynucleotides. The sequencing primers can bind to the first sequencing primer target 426 and/or the second sequencing primer target 428 to add complementary nucleotides to the second sequence of nucleotides 420.

In some cases, the first sequencing primer target 426 and the second sequencing primer target 428 can include a same sequence of nucleotides, while in other situations, the first sequencing primer target 426 and the second sequencing primer target 428 can include different sequences of nucleotides. In various implementations, the first sequencing primer target 426 and the second sequencing primer target 428 can include sequences of nucleotides that are different from the payload 404, the first file identifier 408, the second file identifier 410, and/or the modified calibration region 422. The third sequence of nucleotides 430 can be synthesized during the sequencing process.

At 432, the process 400 can include adding adapters to the third sequence of nucleotides 430, such as a first adapter 434 and a second adapter 436, to produce a fourth sequence of nucleotides 438. The first adapter 434 and the second adapter 436 can include sequences of nucleotides to attach the fourth sequence of nucleotides 438 to a surface of a sequencing machine, such as a surface of a flow cell, during the sequencing process. In some cases, the first adapter 434 and the second adapter 436 can include a same sequence of nucleotides, while in other situations, the first adapter 434 and the second adapter 436 can include different sequences of nucleotides. In various implementations, the first adapter 434 and the second adapter 436 can include sequences of nucleotides that are different from the payload 404, the first file identifier 408, the second file identifier 410, the modified calibration region 422, the first sequencing primer target 426, and the second sequencing primer target 428. The fourth sequence of nucleotides 438 can be synthesized during the sequencing process.

Although the illustrative example of FIG. 4 shows sequences of nucleotides 412, 420, 430, 438 having a number of different regions of nucleotides, the sequences of nucleotides 412, 420, 430, 438 can include additional regions. For example, the sequences of nucleotides 412, 420, 430, 438 can include one or more regions of nucleotides that correspond to location information that indicates a location of bits encoded by a respective payload within a larger string of bits. In another example, the sequences of nucleotides 412, 420, 430, 438 can include one or more regions of nucleotides that correspond to error correction information that can be used to correct errors that may occur during polynucleotide replication and amplification operations that take place during the retrieval of digital data encoded by polynucleotides. In addition, although the modifications have been described in the illustrative example of FIG. 4 with respect to the first calibration region 412, similar modifications can be made to the second calibration region 414 in addition to the changes made to the first calibration region 414 or alternatively to the changes made to the first calibration region 412.

Figure 5:
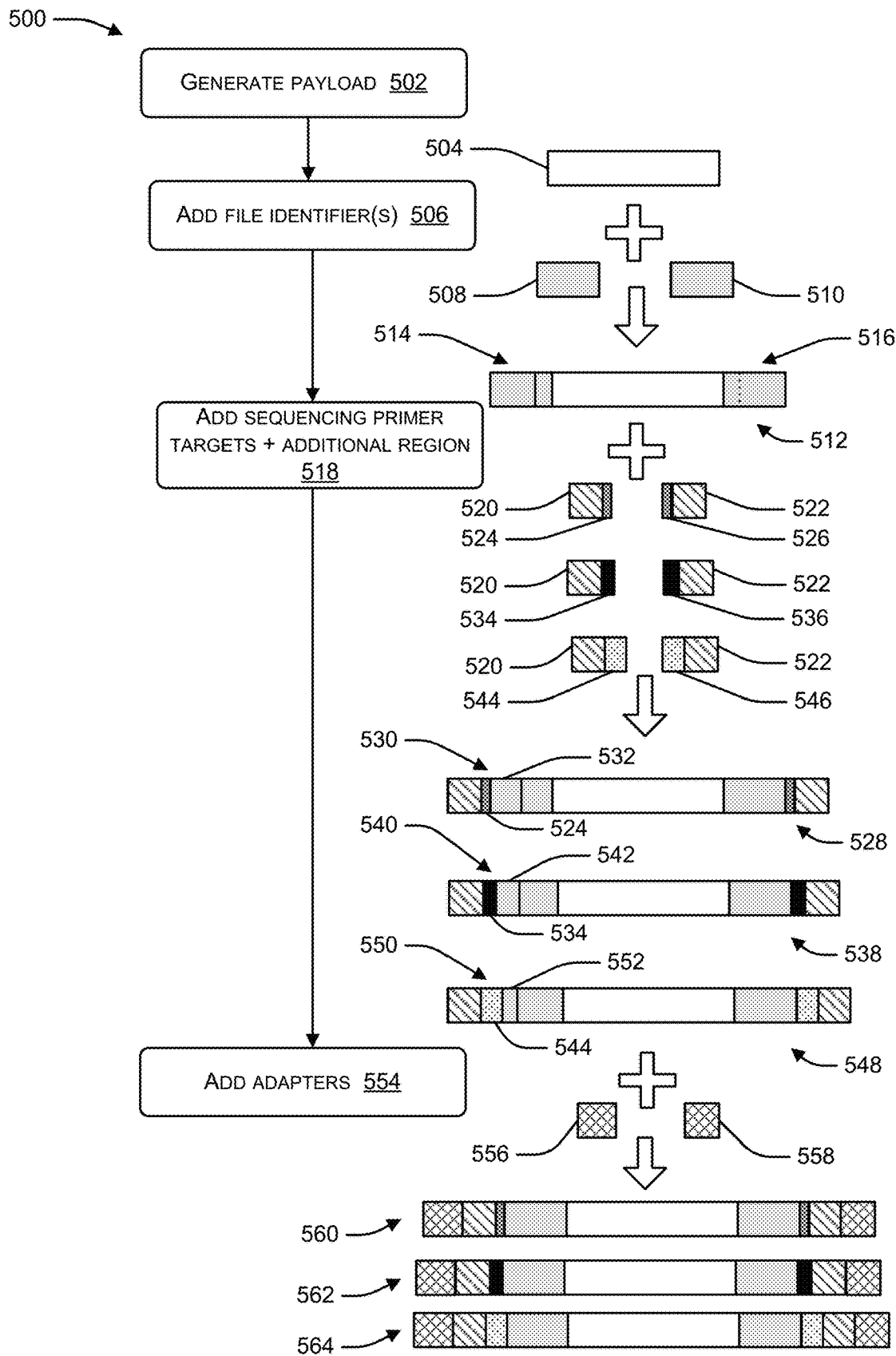
FIG. 5 shows a flow diagram of an example process to modify calibration regions of polynucleotides by adding regions of varying length to the polynucleotides.

FIG. 5 is a schematic diagram of a process 500 to modify a calibration region of a polynucleotide by producing polynucleotides of varying length. At 502, the process 500 can include generating a payload 504. The payload 504 can include a sequence of nucleotides that encodes digital data. Data corresponding to the payload 504 can be generated by a computing device using an encoding scheme that correlates bits of the digital data with nucleotides. In some implementations, the payload 504 can be synthesized after the data corresponding to the payload 504 is generated by the computing device.

At 506, the process 500 can include adding one or more file identifiers to the payload 504. In the illustrative example of FIG. 5, two file identifiers are added to the payload 504, a first file identifier 508 and a second file identifier 510, to produce a first sequence of nucleotides 512. In some cases, the first file identifier 508 and the second file identifier 510 can include a same sequence of nucleotides. In other situations, the first file identifier 508 and the second file identifier 510 can include different sequences of nucleotides. In various implementations, data corresponding to the file identifiers 508 and 510 can be generated and data corresponding to the first sequence of nucleotides 512 can be generated by a computing device before synthesizing the first sequence of nucleotides 512.

In particular implementations, the first file identifier 508 and/or the second file identifier 510 can have the same nucleotide at one or more positions with file identifiers of other payloads that may be sequenced with the payload 504. The number of positions of the file identifiers and/or the number of polynucleotides including the file identifiers having the same nucleotide at one or more positions as the first file identifier 508 and/or the second file identifier 510 can be at least a threshold number of positions and/or at least a threshold number of polynucleotides. The threshold number of positions and/or the threshold number of polynucleotides can correspond to a particular likelihood of errors occurring during a sequencing calibration process.

Additionally, in some implementations, at least a portion of the first file identifier 508 and/or the second file identifier 510 can include primer targets. That is, at least a portion of the first file identifier 508 and/or the second file identifier 510 can include sequences of nucleotides that primers can couple with during polynucleotide replication and amplification operations, such as during one or more PCR processes. The primers related to the first file identifier 508 and/or the second file identifier 510 can be utilized in PCR processes that are not performed during the sequencing of the polynucleotides. For example, primers related to the first file identifier 508 and/or the second file identifier 510 can be utilized during the retrieval of polynucleotides corresponding to digital data before sequencing takes place.

The first sequence of nucleotides 512 can include a first calibration region 514 that can comprise at least a portion of the nucleotides of the first file identifier 508. Additionally, or alternatively, the first sequence of nucleotides 512 can include a second calibration region 516 that can comprise at least a portion of the nucleotides of the second file identifier 510. The first calibration region 514 and/or the second calibration region 516 can correspond to a number of nucleotides used by a sequencing machine during a calibration process for the sequencing machine. In some cases, the first calibration region 514 and the second calibration region 516 can include a same number of nucleotides. Additionally, the number of nucleotides included in the first calibration region 514 and/or the second calibration region 516 can be based at least partly on a manufacturer of the sequencing machine, a sequencing technology utilized by the sequencing machine, or both.

At 518, the process 500 can include adding sequencing primer targets having additional regions of different sizes to produce polynucleotides having varying lengths. In the illustrative example of FIG. 5, a first sequencing primer target 520 and a second sequencing primer target 522 can be added to the first sequence of nucleotides 512. The first sequencing primer target 520 and the second sequencing primer target 522 can include sequences of nucleotides used to replicate and amplify polynucleotides during a sequencing process. The first sequencing primer target 520 and the second sequencing primer target 522 can include sequences of nucleotides used to replicate and amplify polynucleotides during a sequencing process. In particular, the first sequencing primer target 520 and the second sequencing primer target 522 can include sequences of nucleotides that are complementary to sequencing primers used to amplify and replicate polynucleotides. The sequencing primers can bind to the first sequencing primer target 520 and/or the second sequencing primer target 522 to add complementary nucleotides to the first sequence of nucleotides 512

In some cases, the first sequencing primer target 520 and the second sequencing primer target 522 can include a same sequence of nucleotides, while in other situations, the first sequencing primer target 520 and the second sequencing primer target 522 can include different sequences of nucleotides. In various implementations, the first sequencing primer target 520 and the second sequencing primer target 522 can include sequences of nucleotides that are different from the payload 504, the first file identifier 508, and/or the second file identifier 510.

In the illustrative example of FIG. 5, the sequencing primers 520, 522 can be coupled with extender sequences that can be used to produce polynucleotides of varying lengths. The extender sequences can include one or more nucleotides. In some examples, the first sequencing primer target 520 can be coupled with a first extender sequence 524 and the second sequencing primer target 522 can be coupled with a second extender sequence 526 to produce a second sequence of nucleotides 528. The first extender sequence 524 and the second extender sequence 526 can include a same number of nucleotides in some cases, while in other situations, the first extender sequence 524 and the second extender sequence 526 can include a different number of nucleotides. The third sequence of nucleotides 528 can include a calibration region 530 that includes the first extender sequence 524 and a first truncated sequence 532 of the first calibration region 514. The number of nucleotides included in the first truncated sequence 532 can include a number of nucleotides of the first calibration region 514 minus the number of nucleotides of the first extender sequence 524. Although not shown in the illustrative example of FIG. 5, the second sequence of nucleotides 528 can include another calibration region that includes the second extender sequence 526 and a truncated portion of the second calibration region 516.

In other examples, the first sequencing primer target 520 can be coupled with a third extender sequence 534 and the second sequencing primer target 522 can be coupled with a fourth extender sequence 536 to produce a third sequence of nucleotides 538. The third extender sequence 534 and the fourth extender sequence 536 can include a same number of nucleotides in some cases, while in other situations, the third extender sequence 534 and the fourth extender sequence 536 can include a different number of nucleotides. The third extender sequence 534 and the fourth extender sequence 536 can include a different number of nucleotides than the first extender sequence 524 and the second extender sequence 526. In various implementations, the third extender sequence 534 and the fourth extender sequence 536 can include a greater number of nucleotides than the first extender sequence 524 and the second extender sequence 526.

The fourth sequence of nucleotides 538 can include a calibration region 540 that includes the third extender sequence 534 and a second truncated sequence 542 of the first calibration region 514. The number of nucleotides included in the second truncated sequence 542 can include a number of nucleotides of the first calibration region 514 minus the number of nucleotides of the third extender sequence 534. Although not shown in the illustrative example of FIG. 3, the third sequence of nucleotides 538 can include another calibration region that includes the fourth extender sequence 536 and a truncated portion of the second calibration region 516.

In additional examples, the first sequencing primer target 520 can be coupled with a fifth extender sequence 544 and the second sequencing primer target 522 can be coupled with a sixth extender sequence 546 to produce a fourth sequence of nucleotides 548. The fifth extender sequence 544 and the sixth extender sequence 546 can include a same number of nucleotides in some cases, while in other situations, the fifth extender sequence 544 and the sixth extender sequence 546 can include a different number of nucleotides. The fifth extender sequence 544 and the sixth extender sequence 546 can include a different number of nucleotides than the first extender sequence 524, the second extender sequence 526, the third extender sequence 534, and/or the fourth extender sequence 536. In various implementations, the fifth extender sequence 544 and the sixth extender sequence 546 can include a greater number of nucleotides than the first extender sequence 524, the second extender sequence 526, the third extender sequence 534, and/or the fourth extender sequence 536. Also, in particular implementations, the arrangements of nucleotides in the extender sequences 524, 526, 534, 536, 544, 546 can be different. To illustrate, the order and number of nucleotides (e.g., A, T, G, C for DNA and T, U, G, C for RNA) can be different for at least a portion of the extender sequences 524, 526, 534, 536, 544, 546.

The fourth sequence of nucleotides 548 can include a calibration region 550 that includes the fifth extender sequence 544 and a third truncated sequence 552 of the first calibration region 514. The number of nucleotides included in the third truncated sequence 552 can include a number of nucleotides of the first calibration region 514 minus the number of nucleotides of the fifth extender sequence 544. Although not shown in the illustrative example of FIG. 5, the fourth sequence of nucleotides 548 can include another calibration region that includes the sixth extender sequence 546 and a truncated portion of the second calibration region 516.

The second sequence of nucleotides 528, the third sequence of nucleotides 538, and the fourth sequence of nucleotides 548 can have different numbers of nucleotides. The differing lengths between the second sequence of nucleotides 528, the third sequence of nucleotides 538, and the fourth sequence of nucleotides 548 can be based on differing lengths of the extender sequences 524, 526, 534, 536, 544, 546. In the illustrative example of FIG. 5, the fourth sequence of nucleotides 548 can have a greater number of nucleotides than the second sequence of nucleotides 528 and the third sequence of nucleotides 538 and the third sequence of nucleotides 538 can have a greater number of nucleotides than the second sequence of nucleotides 528.

At 554, the process 500 can include adding adapters to the second sequence of nucleotides 528, the third sequence of nucleotides 538, and the fourth sequence of nucleotides 548. For example, a first adapter 556 and a second adapter 558, can be used to produce a fifth sequence of nucleotides 560 from the second sequence of nucleotides 528. Additionally, the first adapter 556 and the second adapter 558 can be used to produce a sixth sequence of nucleotides 562 from the third sequence of nucleotides 538. Further, the first adapter 556 and the second adapter 558 can be used to produce a seventh sequence of nucleotides 564 from the fourth sequence of nucleotides.

The first adapter 556 and the second adapter 558 can include sequences of nucleotides to attach to the fifth sequence of nucleotides 560, the sixth sequence of nucleotides 562, and the seventh sequence of nucleotides 564 to a surface of a sequencing machine, such as a surface of a flow cell, during the sequencing process. In some cases, the first adapter 556 and the second adapter 558 can include a same sequence of nucleotides, while in other situations, the first adapter 556 and the second adapter 558 can include different sequences of nucleotides. In various implementations, the first adapter 556 and the second adapter 558 can include sequences of nucleotides that are different from the payload 504, the first file identifier 508, the second file identifier 510, the first sequencing primer target 520, and the second sequencing primer target 522. The fifth sequence of nucleotides 560, the sixth sequence of nucleotides 562, and the seventh sequence of nucleotides 562 can be synthesized during the sequencing process.

By varying the lengths of the extender sequences 524, 526, 534, 536, 544, 546 the calibration regions of the second sequence of nucleotides 528, the third sequence of nucleotides 538, and the fourth sequence of nucleotides 548 are different. In particular, although the file identifiers 508, 510 are the same for the second sequence of nucleotides 528, the third sequence of nucleotides 538, and the fourth sequence of nucleotides 548, the number of nucleotides of the file identifiers 508, 510 that make up the calibration regions are different. Thus, the new calibration regions of the sequences 528, 538, 548 can have fewer positions with a same nucleotide as other polynucleotides to be sequenced with the sequences 528, 538, 548. Additionally, fewer polynucleotides to be sequenced with the sequences 528, 538, 548 can have calibration regions that include a same nucleotide at one or more positions as the new calibration regions of the sequences 528, 538, 548.

In an illustrative example, the first extender sequence 524 can include 5 nucleotides, the third extender sequence 534 can include 7 nucleotides, and the fifth extender sequence 544 can include 9 nucleotides. Additionally, the number of positions that have the same nucleotide between the first extender sequence 524, the third extender sequence 534, and the fifth extender sequence 544 can be minimal or there may be no positions of the first extender sequence 524, the third extender sequence 534, and the fifth extender sequence 544 that have a same nucleotide. During the calibration process, for the fifth sequence of nucleotides 560, the sequencing machine can read the first 5 nucleotides of the first extender sequence 524 and then begin reading the nucleotides of the first file identifier 520. For the sixth sequence of nucleotides 562, the sequencing machine can read the first 7 nucleotides of the third extender sequence 534 before reading nucleotides of the first file identifier 520, while for the seventh sequence of nucleotides 564, the sequencing machine can read the first 9 nucleotides of the fifth extender sequence 544 before reading nucleotides of the first file identifier 520. Thus, when the sequencing machine is reading the sixth position of the calibration region of the sequences 560, 562, 564 the first nucleotide of the first file identifier 520 can be read for the fifth sequence of nucleotides 560, the sixth nucleotide of the second extender sequence 534 can be read for the sixth sequence of nucleotides 562, and the sixth nucleotide of the third extender sequence 534 can be read for the seventh sequence of nucleotides 564. Further, when the sequencing machine is reading the eighth position of the calibration region of the sequences 560, 562, 564, the sequencing machine is reading the third nucleotide of the first file identifier 520 for the fifth sequence of nucleotides 560, the first nucleotide of the first file identifier 520 for the sixth sequence of nucleotides 562, and the eighth nucleotide of the third extender sequence 534 for the seventh sequence of nucleotides 564. Thus, instead of simply reading the same nucleotides of the first file identifier 520 at each position of the calibration regions, the sequencing machine is reading a number of different nucleotides at the respective positions of the calibration regions of the sequences 560, 562, 564. Accordingly, the differences between the order of nucleotides of the first extender sequence 524, the third extender sequence 534, and the fifth extender sequence 544 and the differences in the timing of reading the nucleotides of the first file identifier 520 in the sequences 560, 562, 564, cause the number of positions of the calibration regions of the sequences 560, 562, 564 having a same nucleotide to be reduced.

Although the illustrative example of FIG. 5 shows sequences of nucleotides 512, 528, 538, 548, 560, 562, 564 having a number of different regions of nucleotides, the sequences of nucleotides 512, 528, 538, 548, 560, 562, 564 can include additional regions. For example, the sequences of nucleotides 512, 528, 538, 548, 560, 562, 564 can include one or more regions of nucleotides that correspond to location information that indicates a location of bits encoded by a respective payload within a larger string of bits. In another example, the sequences of nucleotides 512, 528, 538, 548, 560, 562, 564 can include one or more regions of nucleotides that correspond to error correction information that can be used to correct errors that may occur during polynucleotide replication and amplification operations that take place during the retrieval of digital data encoded by polynucleotides.

Figure 6:
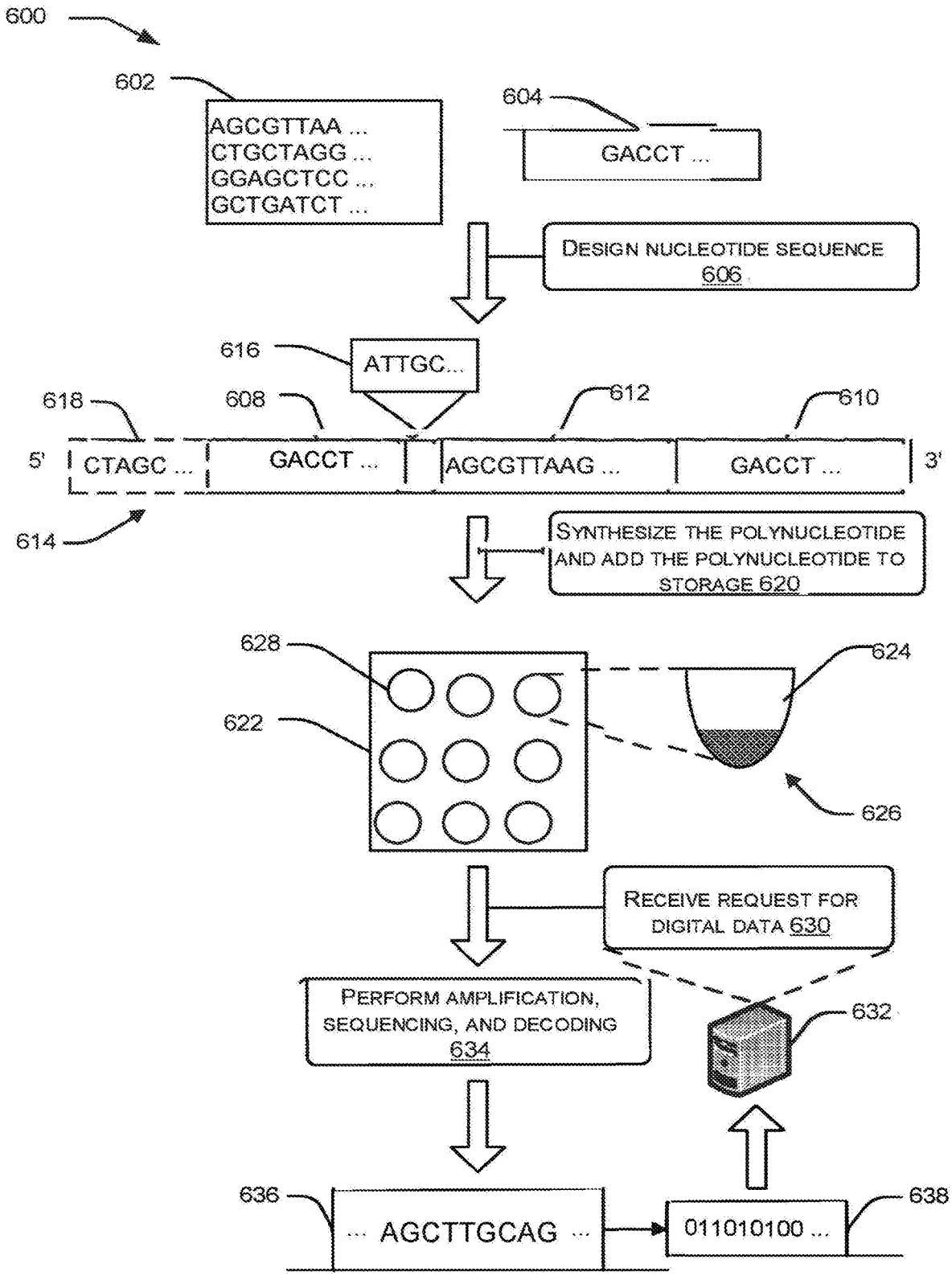
FIG. 6 shows a schematic representation of an example process to generate polynucleotides that have modified calibration regions and to retrieve digital data encoded by the polynucleotides

FIG. 6 shows a schematic representation of an example process 600 to design polynucleotides having less than a threshold likelihood of producing errors during a sequencing calibration process. In particular implementations, the sequence of the polynucleotides can be designed by executing computer-readable instructions of one or more computer software applications. The polynucleotides can be designed using a number of payloads 602 and at least one file identifier 604. The number of payloads 602 can encode data from one or more digital files. At 606, a nucleotide sequence can be designed by associating a first file identifier 608 and a second file identifier 610 with a payload 612 to produce a polynucleotide 614. Although the first file identifier 608 and the second file identifier 610 include the same sequence of nucleotides in the illustrative example of FIG. 6, in other implementations, the first file identifier 608 and the second file identifier 610 can have different sequences of nucleotides. The first file identifier 608 can be placed at a 5' end of the polynucleotide 614 and the second file identifier 610 can be placed at a 3' end of the polynucleotide 614.

In some implementations, additional nucleotides 616 can be included in the polynucleotide 614, where the additional nucleotides 616 encode additional information. For example, at least a portion of the additional nucleotides 616 can encode addressing information. In another example, at least a portion of the additional nucleotides 616 can encode error correction information. Although the position of the additional nucleotides 616 is shown between the first file identifier 608 and the payload 612, the additional nucleotides 616 can be positioned at one or more different positions of the polynucleotide 614.

The polynucleotide 614 can optionally include an additional region 618. The additional region 618 can include a sequence of nucleotides that modifies a calibration region of the polynucleotide 614. In some cases, the additional region 618 can replace a calibration region of the polynucleotide 614. For example, instead of a sequencing machine reading a number of nucleotides of the first identifier 608 during a calibration process, the sequencing machine can read at least a portion of the nucleotides of the additional region 618. In other implementations, the additional region 618 can be utilized to modify a length of the polynucleotide 614 in situations where the polynucleotide 614 is sequenced in conjunction with other polynucleotides that have varying lengths. In these implementations, instead of the calibration region of the polynucleotide 614 including a number of nucleotides of the first file identifier 608, the calibration region of the polynucleotide 614 can include the additional region 618 and fewer nucleotides of the first file identifier 608. Although not shown in the illustrative example of FIG. 6, the polynucleotide 614 can include another additional region coupled with the second file identifier 610 that modifies an additional calibration region on the 3' end of the polynucleotide 614.

At 620, the process 600 includes synthesizing the polynucleotide 614 and adding the polynucleotide 614 to a polynucleotide storage system 622. Synthesizing the polynucleotide 614 can include chemically bonding the nucleotides of the polynucleotide 614 together in a linear chain. The polynucleotide storage system 622 can include a number of containers, such as container 624. Container 624 can include a medium 626 that stores a number of different polynucleotides. The medium 626 can include any medium that can maintain the chemical bonding and structure of polynucleotides over an extended period of time, such as several years, several decades, or longer. In some implementations, the medium 626 can include water. In some implementations, the polynucleotide storage system 622 can store polynucleotide sequences using a media free arrangement, such as storing dried polynucleotide pellets.

In some implementations, the container 624 can store a number of polynucleotides. Also, the container 624 can store multiple copies of a polynucleotide, such as the polynucleotide 614. Additionally, in various implementations, more than one of the containers of the polynucleotide storage system 622 can store a particular polynucleotide. To illustrate, the container 624 and an additional container 628 of the polynucleotide storage system 622 can each store separate copies of the polynucleotide 614. In some implementations, polynucleotides stored in the container 624 can have melting points within a first range, while polynucleotides stored in the additional container 628 can have melting points within a second range. Thus, the polynucleotides of the container 624 and polynucleotides of the additional container 628 can be stored and retrieved based on their different melting points.

At 630, the process 600 includes receiving a request for digital data. The request for digital data can be received from a computing device, such as computing device 632. After receiving the request for the digital data, the one or more polynucleotides that correspond to the digital data can be determined using a lookup table or other data structure that indicates the polynucleotides that encode the requested digital data. For example, a data structure can indicate that a data file is encoded by a group of polynucleotides and that the group of polynucleotides are associated with respective file identifiers. The file identifiers can correspond with primers that can be used to amplify and replicate the polynucleotides stored by the polynucleotide storage system 622. In some implementations, the primers used to replicate and amplify the polynucleotides stored by the polynucleotide storage system 622 can be complementary to the file identifiers of the polynucleotides. In this way, the primers that correspond to the file identifiers can be used to selectively amplify and replicate the polynucleotides corresponding to the digital data being requested.

At 634, the process 600 can include amplification of polynucleotides corresponding to the requested digital data using primers associated with the polynucleotides, sequencing of the polynucleotides produced from the amplification operation, and decoding the polynucleotides to produce the requested digital data. In some implementations, the primers and enzymes used to replicate the target polynucleotides can be added to one or more containers of the polynucleotide storage system 622 or to one or more other containers that include the polynucleotides that correspond to the requested digital data.

In an illustrative example, PCR can be used to amplify the polynucleotides that correspond to the requested digital data. PCR can also be utilized during the sequencing of the polynucleotides. A PCR reaction has three main components: the template, the primers, and enzymes. The template is a single- or double-stranded molecule containing the (sub)sequence of nucleotides to be amplified. The primers are short synthetic strands that define the beginning and end of the region to be amplified. The enzymes include polymerases and thermostable polymerases such as DNA polymerase, RNA polymerase and reverse transcriptase. The enzymes create double-stranded polynucleotides from a single-stranded template by "filling in" complementary nucleotides one by one through addition of nucleoside triphosphates, starting from a primer bound to that template. PCR happens in "cycles," each of which doubles the number of templates in a solution. The process can be repeated until the desired number of copies is created.

A variety of PCR techniques are known and can be used in the implementations described herein. PCR techniques are typically used for the amplification of at least a portion of a polynucleotide. The sample to be amplified is contacted with the first and second primers; a nucleic acid polymerase; and nucleotide triphosphates corresponding to the nucleotides to be added during PCR. Natural nucleotide triphosphates can include dATP, dCTP, dGTP, dTTP, and dUTP. Nucleoside triphosphates of non-standard nucleotides can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

An additional type of PCR is Droplet Digital™ PCR (ddPCR™) (Bio-Rad Laboratories, Hercules, Calif.). ddPCR technology uses a combination of microfluidics and surfactant chemistry to divide PCR samples into water-in-oil droplets. The droplets support PCR amplification of the target template nucleotides they contain and use reagents and workflows similar to those used for most standard Taqman probe-based assays. Following PCR, each droplet is analyzed or read in a flow cytometer to determine the fraction of PCR-positive droplets in the original sample. These data are then analyzed using Poisson statistics to determine the target concentration in the original sample. See Bio-Rad Droplet Digital™ (ddPCR™) PCR Technology.

While ddPCR™ is one PCR approach, other sample partition PCR methods based on the same underlying principles may also be used. The partitioned nucleotides of a sample can be amplified by any suitable PCR methodology that can be practiced within spdPCR. Illustrative PCR types include allele-specific PCR, assembly PCR, asymmetric PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, single-cell PCR, solid-phase PCR, thermal asymmetric interlaced PCR, touchdown PCR, universal fast walking PCR, etc. Ligase chain reaction (LCR) can also be used.

Emulsion PCR can also be utilized in the implementations described herein. Emulsion PCR includes providing a water-in-oil emulsion that includes reagents used during the PCR process, such as a polymerase, primers, buffers, and the like. As the PCR process takes place, strands of the polynucleotides are replicated within the oil droplets using a polymerase and then denatured. The process continues for multiple cycles with replication of the new single stranded polynucleotides taking place within the droplets. The polynucleotides that have been produced during emulsion PCR can be recovered after breaking the emulsion and performing one or more separation processes. In some cases, beads can be used in emulsion PCR where polynucleotides bind to the surface of the beads within the emulsion and the replication of the polynucleotides takes place on the surface of the beads.

The amplification of polynucleotides can be performed using a thermocycler. A thermocycler (also known as a thermal cycler, PCR machine, or DNA amplifier) can be implemented with a thermal block that has holes where tubes holding an amplification reaction mixture can be inserted. The term "amplification reaction mixture" can refer to an aqueous solution comprising the various reagents used to amplify a target nucleic acid. The thermocycler can then raise and lower the temperature of the block in discrete, pre-programmed steps. Other implementations can utilize a miniaturized thermocycler in which the amplification reaction mixture moves via a channel through hot and cold zones on a microfluidic chip.

After the amplification process, one or more samples of the amplification product can be extracted and sequenced by a sequencing machine. In various implementations, the calibration regions of polynucleotides can be modified during the sequencing operations. In other implementations, the calibration regions of the polynucleotides may have been modified prior to the sequencing process. The sequencing machine can provide raw sequence data output referred to herein as reads. Each position in a read is an individual nucleotide determined by the sequencing machine based on properties of the nucleotides sensed by components of the sequencing machine. A read can represent a determination of which of the four nucleotides—A, G, C, and T (or U)—in a strand of DNA (or RNA) is present at a given position in the sequence. The sequencing machine can produce polynucleotide data 636 that corresponds to the sequences of the polynucleotides read by the sequencing machine. The polynucleotide data 636 can be decoded using a reverse process that was used to encode the original digital data to produce a bit string 638 that corresponds to the original digital data being requested. The bit string 638 can be provided to the computing device 632 in response to the request for the digital data.

Figure 7:
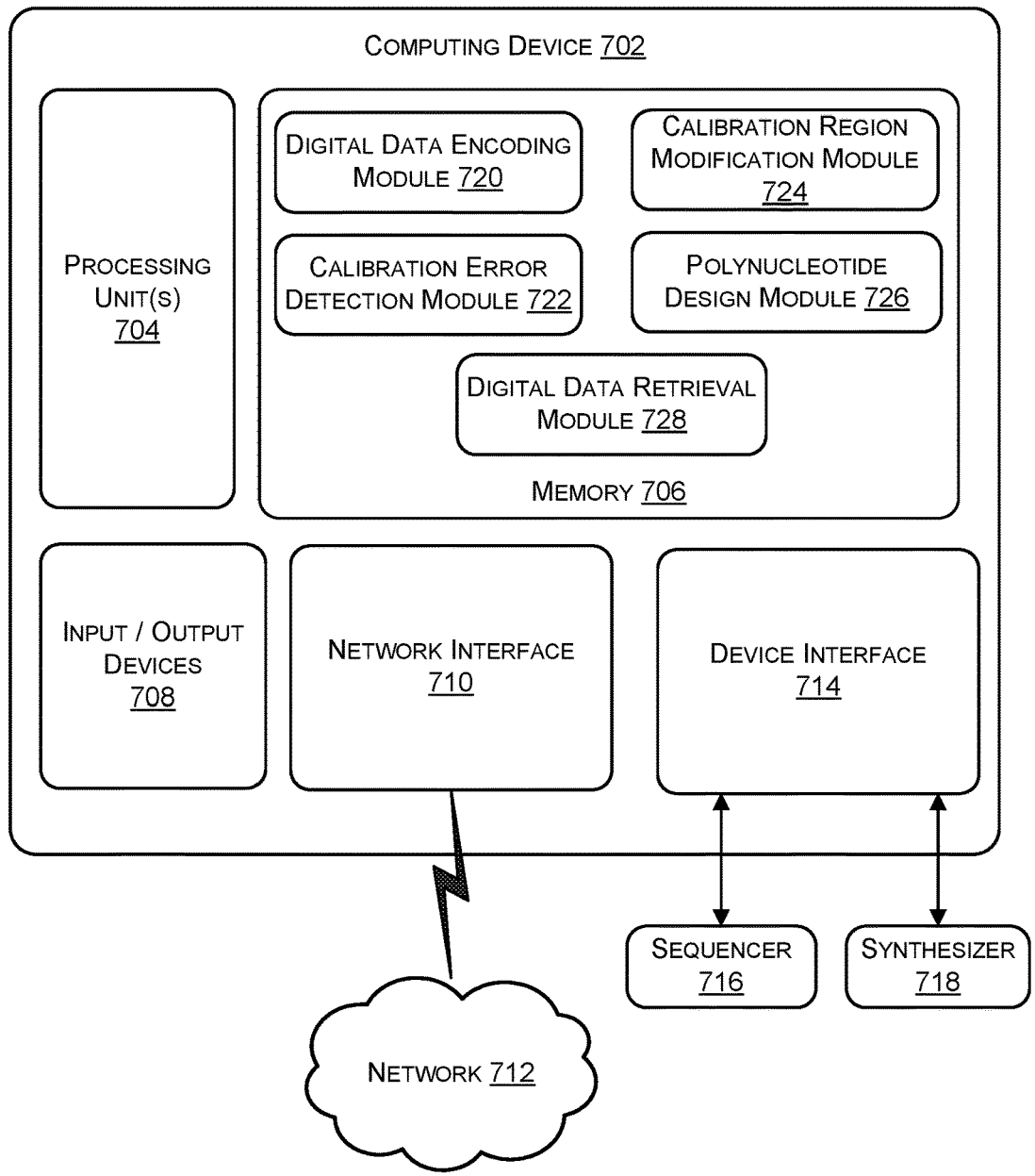
FIG. 7 shows a block diagram of an example computing device to produce polynucleotides having modified calibration regions.

FIG. 7 shows a block diagram of an example system 700 including a computing device 702 to generate data corresponding to polynucleotides used to store digital data. The computing device 702 can be implemented with one or more processing unit(s) 704 and memory 706, both of which can be distributed across one or more physical or logical locations. For example, in some implementations, the operations described as being performed by the computing device 702 can be performed by multiple computing devices. In some cases, the operations described as being performed by the computing device 702 can be performed in a cloud computing architecture.

The processing unit(s) 704 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 704 can use Single Instruction Multiple Data (SIMD) parallel architecture. For example, the processing unit(s) 704 can include one or more GPUs that implement SIMD. One or more of the processing unit(s) 704 can be implemented as hardware devices. In some implementations, one or more of the processing unit(s) 704 can be implemented in software and/or firmware in addition to hardware implementations. Software or firmware implementations of the processing unit(s) 704 can include computer- or machine-executable instructions written in any suitable programming language to perform the various functions described. Software implementations of the processing unit(s) 704 may be stored in whole or part in the memory 706.

Alternatively, or additionally, the functionality of computing device 702 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 706 of the computing device 702 can include removable storage, non-removable storage, local storage, and/or remote storage to provide storage of computer-readable instructions, data structures, program modules, and other data. The memory 706 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device 702 can include and/or be coupled with one or more input/output devices 708 such as a keyboard, a pointing device, a touchscreen, a microphone, a camera, a display, a speaker, a printer, and the like. Input/output devices 708 that are physically remote from the processing unit(s) 704 and the memory 706 can also be included within the scope of the input/output devices 708.

Also, the computing device 702 can include a network interface 710. The network interface 710 can be a point of interconnection between the computing device 702 and one or more networks 712. The network interface 710 can be implemented in hardware, for example, as a network interface card (NIC), a network adapter, a LAN adapter or physical network interface. The network interface 710 can be implemented in software. The network interface 710 can be implemented as an expansion card or as part of a motherboard. The network interface 710 can implement electronic circuitry to communicate using a specific physical layer and data link layer standard, such as Ethernet or Wi-Fi. The network interface 710 can support wired and/or wireless communication. The network interface 710 can provide a base for a full network protocol stack, allowing communication among groups of computers on the same local area network (LAN) and large-scale network communications through routable protocols, such as Internet Protocol (IP).

The one or more networks 712 can include any type of communications network, such as a local area network, a wide area network, a mesh network, an ad hoc network, a peer-to-peer network, the Internet, a cable network, a telephone network, a wired network, a wireless network, combinations thereof, and the like.

A device interface 714 can be part of the computing device 702 that provides hardware to establish communicative connections to other devices, such as a sequencer 716, a polynucleotide synthesizer 718, etc. The device interface 714 can also include software that supports the hardware. The device interface 714 can be implemented as a wired or wireless connection that does not cross a network. A wired connection may include one or more wires or cables physically connecting the computing device 702 to another device. The wired connection can be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like.

The computing device 702 can include multiple modules that may be implemented as instructions stored in the memory 706 for execution by processing unit(s) 704 and/or implemented, in whole or in part, by one or more hardware logic components or firmware. The memory 706 can be used to store any number of functional components that are executable by the one or more processing units 704. In many implementations, these functional components comprise instructions or programs that are executable by the one or more processing units 704 and that, when executed, implement operational logic for performing the operations attributed to the computing device 702. Functional components of the computing device 702 that can be executed on the one or more processing units 704 for implementing the various functions and features related to generating polynucleotide sequences for the storage and retrieval of digital data, as described herein, include a digital data encoding module 720, a calibration error detection module 722, a calibration region modification module 724, a polynucleotide design module 726, and a digital data retrieval module 728. One or more of the modules, 720, 722, 724, 726, 728 can be used to implement processes 100, 200, 300, 400, 500 and at least a portion of the process 600 of FIG. 1, FIG. 2, FIG. 3, FIG. 4, FIG. 5, and FIG. 6.

The digital data encoding module 720 can include computer-readable instructions that are executable by the processing unit(s) 704 to encode digital data as a sequence of nucleotides. The digital data encoding module 720 can obtain digital data from one or more sources. In some cases, the digital data can also be stored by the memory 706. Also, the digital data can be stored by a data storage device coupled to, or otherwise accessible to, the computing device 702. The digital data can be related to image content, video content, text content, audio content, combinations thereof, and so forth. The digital data can include a bit string comprised of 1s and 0s.

The digital data encoding module 720 can encode the 1s and 0s of the digital data to a sequence of nucleotides, such as A, T, G, C, or U. In particular implementations, each 1 or 0 of the digital data can be encoded as a particular nucleotide. In some cases, groups of 1s and groups of 0s of the digital data can be encoded as a particular nucleotide. In various implementations, the 1s and 0s of the digital data can be converted to a number in a number system other than base 2 before encoding. For example, the 1s and 0s of the digital data can be converted to a base-3 format or a base-4 format before encoding.

In illustrative implementations, the digital data encoding module 720 can encode the 1s and 0s of the digital data according to a binary encoding scheme. For example, the digital data encoding module 720 can encode the series of bits 00 as a first nucleotide (e.g., A), the series of bits 01 as a second nucleotide (e.g., T), the series of bits 10 as a third nucleotide (e.g., G), and the series of bits 11 as a fourth nucleotide (e.g., C).

In other illustrative implementations, the digital data encoding module 720 can encode the 1s and 0s of the digital data according to a ternary encoding scheme. For example, the digital data encoding module 720 can convert the 1s and 0s of the digital data to modified digital data comprising 0s, 1s, and 2s. Subsequently, the digital data encoding module 720 can encode the 0s, 1s, and 2s of the modified digital data as nucleotides. In some implementations, the data encoding module 720 can encode the 0s, 1s, and 2s of the modified digital data as nucleotides according to a preceding nucleotide in the sequence of nucleotides. To illustrate, a 0 preceded by G could be encoded as T, while a 0 preceded by A could be encoded as C.

In additional illustrative implementations, the digital data encoding module 720 can encode the 1s and 0s of the digital data according to a base-4 encoding scheme. In an example, the digital data encoding module 720 can convert the 1s and 0s of the digital data to modified digital data comprising 0s, 1s, 2s, and 3s. In these situations, when 4 nucleotides are used to encoded the digital data, each type of nucleotide being used to do the encoding can correspond with a respective base-4 number. Thus, in a particular illustrative example, 0 can correspond with A, 1 can correspond with T, 2 can correspond with G, and 3 can correspond with C.

In some cases, the length of the sequences of nucleotides encoding the digital data can be limited. For example, if the length of the sequence of nucleotides encoding the digital data is greater than a particular number of nucleotides, the sequence can become unstable and/or otherwise lose its linear arrangement, such as by forming secondary structures. In illustrative implementations, the sequences of nucleotides used to encode digital data can have from 60 to 150 nucleotides, from 80 to 130 nucleotides, from 90 to 120 nucleotides, or from 100 to 140 nucleotides. In situations where multiple sequences are used to encode the digital data, the digital data encoding module 720 can divide the bits of the digital data into segments. The digital data encoding module 720 can encode each of the segments of the digital data as a separate sequence of nucleotides. In some cases, the segments can be the same length, while in other situations, the segments can have varying lengths. In various implementations, segmenting the nucleotides encoding digital data can reduce the number of steps performed during sequencing of polynucleotides because the segmenting that is typically performed during sequencing can be avoided.

The calibration error detection module 722 can include computer-readable instructions that, when executed by the processing unit(s) 704, can determine a likelihood that an error may take place during a sequencing calibration process. In particular implementations, the likelihood of an error taking place during a sequencing calibration process can correspond to a threshold probability of an error occurring during the sequencing calibration process, such as 90%, 95%, or 99%. In various implementations, the calibration error detection module 722 can determine a number of positions of calibration regions of polynucleotides to be sequences that have a same nucleotide. The calibration regions can include a number of nucleotides read by a sequencing machine during a calibration process. The calibration regions can be located on 5' ends of polynucleotides, 3' ends of polynucleotides, or both the 5' ends and the 3' ends of the polynucleotides. In some implementations, the calibration error detection module 722 can utilize a BLAST algorithm to compare nucleotides at individual positions included in calibration regions of polynucleotides to be sequenced. The calibration error detection module 722 can also determine a number of polynucleotides having a same nucleotide at one or more positions of their respective calibration regions. Additionally, the calibration error detection module 722 can determine a distribution of each type of nucleotide at individual positions of the calibration regions of polynucleotides to be sequenced.

In particular implementations, the calibration error detection module 722 can compare a nucleotide located at a first position of a calibration region of a first polynucleotide with a nucleotide located at the first position of a calibration region of a second polynucleotide. Continuing with this example, the calibration error detection module 722 can determine that the first polynucleotide and the second polynucleotide have a same nucleotide at the first position of their calibration regions. That is, the calibration error detection module 722 can determine that the calibration regions of the first polynucleotide and the second polynucleotide both have A at the first position, C at the first position, T (or U in the case of RNA) at the first position, or G at the first position. Thus, the calibration error detection module 722 can determine a number of matches between nucleotides at respective positions of polynucleotides to be sequenced. In an illustrative example, an amount of sequence identity between a first polynucleotide and a second polynucleotide can indicate that the first polynucleotide and the second polynucleotide have the same nucleotide at 1 position of their calibration regions, 2 positions of their calibration regions, 5 positions of their calibration regions, and so forth. In various implementations, the calibration error detection module 722 can determine a number of consecutive positions of calibration regions of polynucleotides where nucleotides match.

The calibration error detection module 722 can also determine a number of polynucleotides that have matching nucleotides at various positions of their calibration regions. For example, the calibration error detection module 722 can determine a number of polynucleotides that have each of the four types of nucleotides (e.g., A, T, G, C for DNA or A, U, G, C for RNA) included in the polynucleotides at individual positions of the calibration regions of the polynucleotides. To illustrate, the calibration error detection module 722 can determine a number of polynucleotides having a first nucleotide at a first position of their calibration regions and a number of polynucleotides that have a second nucleotide at a first position of their calibration regions. In another illustrative example, the calibration error detection module 722 can determine a number of polynucleotides having a first nucleotide at each position of the calibration region and a number of polynucleotides having a second nucleotide at each position of the calibration region.

In particular implementations, the calibration error detection module 722 can determine a distribution of each nucleotide at each position of the calibration regions of the polynucleotides to be sequenced. In some examples, the calibration error detection module 722 can determine that a first position of the calibration regions comprise a first amount of a first nucleotide, a second amount of a second nucleotide, a third amount of a third nucleotide, and a fourth amount of a fourth nucleotide. The calibration error detection module 722 can proceed to determine respective amounts of each nucleotide at subsequent positions of the calibration regions of the polynucleotides to be sequenced.

The calibration error detection module 722 can determine a likelihood that an error may occur during a sequencing calibration process based at least in part on a number of positions of calibration regions of polynucleotides to be sequenced that have a same nucleotide, a number of polynucleotides having the same nucleotide at one or more positions of their calibration regions, a distribution of one or more nucleotides at one or more positions of the calibration regions of the polynucleotides to be sequenced, or combinations thereof. The calibration error detection module 722 can utilize a number of thresholds to determine a likelihood that an error may occur during a sequencing calibration process. For example, the calibration error detection module 722 can utilize a threshold number of polynucleotides that have the same nucleotide at one or more positions of their calibration regions to determine a likelihood that an error may occur during a sequencing calibration process. The calibration error detection module 722 can also utilize a threshold number of positions at which a threshold number of polynucleotides have a same nucleotide to determine a likelihood that an error may occur during a sequencing calibration process. The calibration error detection module 722 can also utilize a threshold difference between an expected distribution of one or more nucleotides at each position of a calibration region of polynucleotides to be sequenced and an actual distribution of the one or more nucleotides at each of the positions.

In various implementations, the calibration error detection module 722 can determine that a likelihood of an error occurring during a sequencing calibration process is greater than a threshold percentage based at least partly on determining that at least a threshold number of polynucleotides have the same nucleotide at one or more positions of their calibration regions. For example, the calibration error detection module 722 can determine that there is at least a 90% probability that an error may occur during a sequencing calibration process based at least partly on determining that at least 10,000 polynucleotides have a same nucleotide at one or more positions of their calibration regions. In a particular illustrative example, the calibration error detection module 722 can determine that there is at least a 90% probability of an error occurring during a sequencing calibration process based at least partly on determining that at least 10,000 polynucleotides have A at the second position of their calibration regions.

In addition, the calibration error detection module 722 can determine that a likelihood of an error occurring during a sequencing calibration process is greater than a threshold percentage based at least partly on at least a threshold number of positions of the calibration regions of polynucleotides to be sequenced at which at least a threshold number of the polynucleotides have the same nucleotide. For example, the calibration error detection module 722 can determine that there is at least a 90% probability of an error occurring during a sequencing calibration process based at least partly on determining that at least 10,000 polynucleotides have at least three positions in their calibration regions that are a same nucleotide. In a particular illustrative example, the calibration error detection module 722 can determine that there is at least a 90% probability of an error occurring during a sequencing calibration process based at least partly on determining that at least 10,000 polynucleotides have A in a first position of their calibration regions, G in a third position of their calibration regions, and C in a sixth position of their calibration regions.

Further, the calibration error detection module 722 can determine that a likelihood of an error occurring during a sequencing calibration process is at least a threshold percentage based at least partly on an expected distribution of at least one nucleotide located in at least one position of a threshold number of polynucleotides being at least a threshold amount different from an actual distribution of the at least one nucleotide located in the at least one position. For example, the calibration error detection module 722 can determine that there is at least a 90% probability of an error occurring during a sequencing calibration process based at least partly on determining that at least 10,000 nucleotides have a distribution of at least one nucleotide at a particular position of their calibration regions that is at least 5% different from an expected distribution. In a particular illustrative example, the calibration error detection module 722 can determine that there is at least a 90% probability of an error occurring during a sequencing calibration process based at least partly on determining that at least 10,000 nucleotides have a distribution of 40% As at a third position of their calibration regions with respect to an expected distribution of As at the third position being from 20% to 30%. Thus, in this particular illustrative example, the difference between the expected distribution and the actual distribution of the nucleotide A at the third position is 10%, which is at least the threshold difference of 5%.

The calibration region modification module 724 can include computer-readable instructions that when executed by the processing unit(s) 704 can modifying sequences of nucleotides in calibration regions of polynucleotides. In some implementations, the calibration region modification module 724 can be invoked based on the calibration error detection module 722 determining at least a threshold probability of an error occurring during a sequencing calibration process. Modifying the calibration regions of the polynucleotides can include adding a region of nucleotides to the polynucleotides. In particular, the calibration region modification module 724 can generate a new calibration region that can be added to a polynucleotide. The new calibration region can have less than a threshold number of positions with a same nucleotide with respect to calibration regions of additional polynucleotides to be sequenced. Additionally, the new calibration regions can have a particular distribution of nucleotides. For example, the calibration region modification module 724 can generate new calibration regions that have from about 20% to about 30% As, from about 20% to about 30% Ts, from about 20% to about 30% Gs, and from about 20% to about 30% Cs. Further, the calibration region modification module 724 can add a region to polynucleotides to produce polynucleotides having varying lengths.

The calibration region modification module 724 can also modify calibration regions of polynucleotides by modifying the arrangement of nucleotides in the calibration regions. In some cases, modifying the arrangement of nucleotides in a calibration region can include modifying an order in which the nucleotides of a calibration region are arranged. That is, the quantity of each type of nucleotide in a calibration region can remain the same, but the order in which the nucleotides are arranged can be modified. In particular implementations, the calibration region modification module 724 can modify the order of nucleotides in a calibration region such that the modified calibration region has less than a threshold number of positions with a same nucleotide with respect to other calibration regions of polynucleotides to be sequenced. In various implementations, the calibration region modification module 724 can modify the nucleotides of calibration regions of polynucleotides according to a predetermined scheme.

The polynucleotide design module 726 can include computer-readable instructions that, when executed by the processing unit(s) 704, generate polynucleotide data that correspond to polynucleotides that encode digital data. The polynucleotide design module 726 can utilize data corresponding to payloads produced by the digital data encoding module 720 to generate the polynucleotide data. The polynucleotide design module 726 can also utilize data corresponding to file identifiers associated with the payloads and new calibration regions and/or modified calibration regions generated by the calibration region modification module 724 to generate polynucleotide data.

The polynucleotide design module 726 can also produce data corresponding to polynucleotide sequences that include nucleotides in addition to the nucleotides comprising the file identifiers, payloads, new calibration regions, and/or modified calibration regions. For example, the polynucleotide design module 726 can include nucleotides in a polynucleotide that correspond with addressing information for the payload. In situations where a string of bits is divided into a number of segments before being encoded as a sequence of nucleotides, addressing information can indicate the segment of the bit string that is being encoded by a particular payload and the location of the segment within the bit string. The polynucleotide design module 726 can generate one or more nucleotides that encode the addressing information and add the nucleotides encoding the addressing information into a polynucleotide. In particular implementations, addressing information can be included, at least partially, in file identifiers. The file identifiers can also include nucleotides that correspond to a key that can be used to retrieve the digital data encoded by a payload of a polynucleotide. The polynucleotides design module 726 can also add nucleotides to a polynucleotide that correspond to error correction information.

The polynucleotide data generated by the polynucleotide design module 726 can be used to synthesize molecules that include the polynucleotides. In some implementations, the polynucleotide design module 726 can communicate polynucleotide sequences to one or more devices, such as polynucleotide synthesizer 718, used to synthesize the polynucleotides. For example, the polynucleotide design module 726 can communicate polynucleotides to a service provider that synthesizes polynucleotides via the one or more networks 712. In another example, the polynucleotide design module 726 can communicate polynucleotides to a device that synthesizes polynucleotides via the one or more networks 712 and/or to one or more devices (e.g., synthesizer 718) via the device interface 714.

The digital data retrieval module 728 can include computer-readable instructions that when executed by the processing unit(s) 704 can provide digital data in response to a request for the digital data. In some implementations, the digital data retrieval module 728 can receive a request to obtain digital data. For example, the digital data retrieval module 728 can receive a request for a data file including a digital image. The digital data retrieval module 728 can identify one or more polynucleotides that correspond to the requested data. To illustrate, the digital data retrieval module 728 can parse a data structure, such as a lookup table, to identify the file identifiers, addressing information, and/or keys that correspond to the requested digital data. The digital data retrieval module 728 can communicate with one or more devices, such as via the device interface 714, to request the polynucleotides that correspond to the file identifiers, addressing information, and/or keys. The digital data retrieval module 728 can receive the polynucleotides from one or more devices, such as polynucleotide synthesizer 718, and decode the polynucleotides using a reverse process from the encoding performed by the digital data encoding module 720. For example, in implementations where 00 in a string of bits is encoded as A, the digital data retrieval module 728 can decode each A in the polynucleotide sequences as 00. The digital data retrieval module 728 can reproduce the bit string of the digital data being requested and provide the bit string to one or more devices that requested the digital data.

In some implementations, the digital data retrieval module 728 can access a memory structure to identify changes to calibration regions of polynucleotides. For example, in situations where modifying the calibration region includes modifying at least a portion of a file identifier, the changes to the file identifier can be tracked in order to recreate the original file identifier after polynucleotide sequencing. In this way, the digital data associated with various polynucleotides having modified calibration regions can be correctly identified and reassembled.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause A. A method comprising: performing an analysis of sequences of a group of polynucleotides, individual polynucleotides of the number of polynucleotides including individual calibration regions comprising a sequence of nucleotides read by a sequencing machine during a calibration process; determining, based at least partly on the analysis, a number of polynucleotides of the group of polynucleotides having a same nucleotide located in a position of calibration regions of the number of polynucleotides; determining that the number of polynucleotides having the same nucleotide located in the position of the individual calibration regions is greater than a threshold number; and modifying a nucleotide sequence of the calibration regions of the number of polynucleotides to produce a modified group of polynucleotides, wherein a number of the modified group of polynucleotides having a same nucleotide at one or more positions of the calibration regions is less than the threshold number.

Clause B. The method of clause A, wherein determining the number of polynucleotides of the group of polynucleotides having the same nucleotide located in the position of the calibration regions of the number of polynucleotides includes: comparing a first nucleotide at the position of a first calibration region of a first polynucleotide of the group of polynucleotides with a second nucleotide at the position of a second calibration region of a second polynucleotide of the group of polynucleotides; and determining that the first nucleotide and the second nucleotide are the same.

Clause C. The method of clause A or B, wherein modifying the nucleotide sequence of the calibration regions of the number of polynucleotides to produce the modified group of polynucleotides is based at least partly on: determining that an additional number of polynucleotides of the group of polynucleotides have a same nucleotide located in at least a threshold number of positions of the calibration regions of the additional number of polynucleotides; and determining that the additional number of polynucleotides is at least the threshold number of positions of the calibration regions.

Clause D. The method of any one of clauses A-C, further comprising: synthesizing the group of polynucleotides to produce a synthesized group of polynucleotides; wherein modifying the calibration regions of the number of polynucleotides is performed with respect to nucleotide sequences of the synthesized group of polynucleotides.

Clause E. The method of clause D, further comprising: adding a first sequencing primer target to a first calibration region of a first synthesized polynucleotide of the synthesized group of polynucleotides to produce a modified first synthesized polynucleotide, the first sequencing primer target having a first extender sequence with a first number of nucleotides; and adding a second sequencing primer target to a second calibration region of a second synthesized polynucleotide of the synthesized group of polynucleotides to produce a modified second synthesized polynucleotide, the second sequencing primer target having a second extender sequence with a second number of nucleotides different from the first number of nucleotides.

Clause F. The method of clause E, wherein: a first modified calibration region of the modified first synthesized polynucleotide includes the first extender sequence and a number of nucleotides of the first calibration region; a second modified calibration region of the modified second synthesized polynucleotide includes the second extender sequence and a number of nucleotides of the second calibration region.

Clause G. The method of any of clauses A-F, further comprising: generating first data that indicates the respective nucleotide sequences of the group of polynucleotides; generating second data that indicates additional nucleotide sequences of the modified group of polynucleotides; and synthesizing, based at least partly on the second data, the modified group of polynucleotides.

Clause H. The method of any of clauses A-G, wherein the group of polynucleotides include deoxyribonucleic acid (DNA) or ribonucleic acid (RNA).

Clause I. The method of any of clauses A-H, wherein: individual polynucleotides of the group of polynucleotides include first regions of nucleotides that encode individual portions of digital data and second regions of nucleotides that include a file identifier corresponding to the digital data; and the individual calibration regions comprise at least a portion of the nucleotides included in the second regions.

Clause J. The method of clause I, wherein determining the number of polynucleotides of the group of polynucleotides having the same nucleotide located in the one or more positions of the calibration regions of the number of polynucleotides includes: determining that a first file identifier of a first polynucleotide of the number of polynucleotides and a second file identifier of a second polynucleotide of the number of polynucleotides is the same.

Clause K. A method comprising: generating polynucleotide data indicating a polynucleotide including a payload and a file identifier, the payload encoding a segment of digital data and the file identifier being associated with the digital data; determining that a position located in a calibration region of the polynucleotide has a same nucleotide as the same position located in additional calibration regions of at least a threshold number of additional polynucleotides, the calibration region and the additional calibration regions including a sequence of nucleotides used by a sequencing machine during a calibration process of the sequencing machine; and modifying a portion of the polynucleotide data corresponding to the calibration region of the polynucleotide to produce a modified polynucleotide having a modified calibration region.

Clause L. The method of clause K, further comprising: generating a plurality of segments of the digital data; encoding individual segments of the plurality of segments as data indicating individual sequences of nucleotides; and generating additional polynucleotide data indicating a plurality of polynucleotides, the plurality of polynucleotides including the polynucleotide and individual polynucleotides of the plurality of polynucleotides including one of the individual sequences of nucleotides and the file identifier.

Clause M. The method of clause K or L, wherein modifying the calibration region includes modifying the polynucleotide data to add one or more nucleotides to at least one of a 5' end of the polynucleotide or a 3' end of the polynucleotide to produce the modified calibration region.

Clause N. The method of any of clauses K-M, wherein the sequencing machine determines a sequence of the polynucleotide by: attaching the polynucleotide to a surface of a flow cell; producing a cluster of the polynucleotide on the surface of the flow cell by replicating the polynucleotide at a location of the surface of the flow cell; attaching a fluorophore-bound nucleotide to complementary nucleotides at a position of individual polynucleotides of the cluster; applying energy to the fluorophore; capturing one or more images of the surface of the flow cell after applying energy to the fluorophore; performing an analysis of the one or more images to determine wavelengths emitted by different locations of the surface of the flow cell; and determining, based at least partly on the analysis, a type of nucleotide at the position based on a distribution of wavelengths of electromagnetic radiation emitted by the fluorophore.

Clause O. The method of any of clauses K-N, wherein modifying the portion of the polynucleotide data corresponding to the calibration region of the polynucleotide includes modifying an order of the nucleotides included in the calibration region.

Clause P. A system comprising: a processing unit; a memory in communication with the processing unit, the memory storing computer-readable instructions that when executed by the processing unit perform operations comprising: performing an analysis of sequences of a group of polynucleotides; determining, based at least partly on the analysis, that a likelihood of an error occurring during a calibration process of a sequencing machine is at least a threshold probability; modifying a plurality of calibration regions of at least a portion of the group of polynucleotides to produce a modified group of polynucleotides having modified calibration regions, individual calibration regions of the plurality of calibration regions comprising a sequence of nucleotides used by the sequencing machine during a calibration process of the sequencing machine.

Clause Q. The system of clause P, wherein individual sequences of the group of polynucleotides include: a payload region that encode a segment of digital data; a file identifier region that encodes a file identifier associated with the digital data; and an individual calibration region that includes at least a portion of the file identifier region.

Clause R. The system of clause P or Q, wherein the operations further comprise: determining changes between a calibration region of a polynucleotide of the group of polynucleotides and a modified calibration region of a modified polynucleotide of the modified group of polynucleotides; and generating a data structure that stores the changes.

Clause S. The system of clause R, wherein the operations further comprise: receiving a request for the digital data; obtaining sequence data from the sequencing machine, the sequence data including a sequence of nucleotides; determining that the sequence of nucleotides corresponds to the modified polynucleotide; accessing the data structure to determine the changes between the modified polynucleotide and the polynucleotide; generating, based on the sequence data and the changes stored in the data structure, polynucleotide data indicating a sequence of the polynucleotide; and decoding the polynucleotide data to produce a series of bits related to a portion of the digital data.

Clause T. The system of any of clauses P-S, wherein determining that the likelihood of an error occurring during the calibration process of the sequencing machine is at least the threshold probability includes at least one of: determining that at least a threshold number of the group of polynucleotides have a same nucleotide located in a position of individual calibration regions of the threshold number of the group of polynucleotides; determining that at least the threshold number of the group of polynucleotides have a same nucleotide located in at least a threshold number of positions of the individual calibration regions of the threshold number of the group of polynucleotides; or determining that a distribution of nucleotides located in at least one position of the individual calibration regions of the group of polynucleotides is outside of a specified distribution of nucleotides.

Clause U: A polynucleotide including: a payload region that encodes digital data; a file identifier region that encodes a file identifier for the digital data; and a calibration region adjacent to the file identifier region, the calibration region including a number of nucleotides having a distribution of from about 20% to about 30% guanine, from about 20% to about 30% cytosine, from about 20% to about 30% thymine, and from about 20% to about 30% adenine, wherein the calibration region includes a sequence of nucleotides read by a sequencing machine during a calibration process of the sequencing machine.

Clause V. The polynucleotide of clause U, wherein the calibration region is located at a 5' end of the polynucleotide.

Clause W. The polynucleotide of clause U, wherein the calibration region is located at a 3' end of the polynucleotide.

Clause X. The polynucleotide of any of clauses U-W, wherein the file identifier region is located between the payload region and the calibration region.

Clause Y. The polynucleotide of clause U, further comprising: an additional file identifier region located adjacent to the payload region, the additional file identifier region encoding an additional file identifier for the digital data; and wherein the file identifier region is located between the payload region and the calibration region.

Clause Z. The polynucleotide of clause Y, wherein the file identifier region and the additional file identifier region include different sequences of nucleotides.

Clause AA. The polynucleotide of clause Y, wherein the file identifier region and the additional file identifier region include a same sequence of nucleotides.

Clause BB: The polynucleotide of any of clauses Y-AA, further comprising: an additional calibration region that includes an additional number of nucleotides having an additional distribution of from about 20% to about 40% guanine, from about 20% to about 40% cytosine, from about 20% to about 40% thymine, and from about 20% to about 40% adenine.

Clause CC: The polynucleotide of clause BB, wherein: the calibration region is located at a 5' end of the polynucleotide; the additional calibration region is located at a 3' end of the polynucleotide; the file identifier is located between the calibration region and the payload region; and the additional file identifier is located between the additional calibration region and the payload region.

Clause DD. A system comprising: means for performing an analysis of sequences of a group of polynucleotides; means for determining, based at least partly on the analysis, that a likelihood of an error occurring during a calibration process of a sequencing machine is at least a threshold probability; and means for modifying a plurality of calibration regions of at least a portion of the group of polynucleotides to produce a modified group of polynucleotides having modified calibration regions, individual calibration regions of the plurality of calibration regions comprising a sequence of nucleotides used by the sequencing machine during a calibration process of the sequencing machine.

Clause EE. The system of clause DD, wherein individual sequences of the group of polynucleotides include: a payload region that encode a segment of digital data; a file identifier region that encodes a file identifier associated with the digital data; and an individual calibration region that includes at least a portion of the file identifier region.

Clause FF. The system of clause DD 16, further comprising: means for determining changes between a calibration region of a polynucleotide of the group of polynucleotides and a modified calibration region of a modified polynucleotide of the modified group of polynucleotides; and means for generating a data structure that stores the changes.

Clause GG. The system of clause FF, further comprising: means for receiving a request for the digital data; means for obtaining sequence data from the sequencing machine, the sequence data including a sequence of nucleotides; means for determining that the sequence of nucleotides corresponds to the modified polynucleotide; means for accessing the data structure to determine the changes between the modified polynucleotide and the polynucleotide; means for generating, based on the sequence data and the changes stored in the data structure, polynucleotide data indicating a sequence of the polynucleotide; and means for decoding the polynucleotide data to produce a series of bits related to a portion of the digital data.

Clause HH. The system of clause FF, further comprising means for determining that at least a threshold number of the group of polynucleotides have a same nucleotide located in a position of individual calibration regions of the threshold number of the group of polynucleotides; means for determining that at least the threshold number of the group of polynucleotides have a same nucleotide located in at least a threshold number of positions of the individual calibration regions of the threshold number of the group of polynucleotides; or means for determining that a distribution of nucleotides located in at least one position of the individual calibration regions of the group of polynucleotides is outside of a specified distribution of nucleotides.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

What is claimed is:

1. A method comprising:
   receiving a plurality of polynucleotide sequences, wherein each of the plurality of polynucleotide sequences includes a calibration region, the calibration region read by a sequencing machine during a calibration process;
   performing an analysis of sequences of the plurality of polynucleotide sequences;
   determining, based at least partly on the analysis, a number of individual polynucleotide sequences of the plurality of polynucleotide sequences having a same nucleotide located in a same position of the calibration region of each of the plurality of polynucleotide sequences;

determining that the number is greater than a threshold number;

modifying a nucleotide sequence of the calibration region of at least one of the plurality of polynucleotide sequences to produce a modified polynucleotide sequence, wherein, after the modifying, the number is less than the threshold number; and providing the modified polynucleotide sequence to a polynucleotide synthesizer.

2. The method of claim 1, wherein determining the number of polynucleotides of the plurality of polynucleotide sequences having the same nucleotide located in the same position of the calibration region includes:

comparing a first nucleotide at the position of a first calibration region of a first polynucleotide sequence of the plurality of polynucleotide sequences with a second nucleotide at the position of a second calibration region of a second polynucleotide sequence of the plurality of polynucleotide sequences; and determining that the first nucleotide and the second nucleotide are the same.

3. The method of claim 1, wherein modifying the nucleotide sequence of the calibration regions of the number of polynucleotides to produce the modified polynucleotide sequence is based at least partly on:

determining that an additional number of polynucleotides of the plurality are polynucleotide sequences that have a same nucleotide located in at least a threshold number of positions of the calibration region of each of the additional number of polynucleotides; and determining that the additional number of polynucleotides is at least the threshold number.

4. The method of claim 1, further comprising:

synthesizing, by the polynucleotide synthesizer, the plurality of polynucleotide sequences to produce a synthesized group of polynucleotides;

wherein modifying the calibration region of the at least one of the plurality of polynucleotide sequences is performed with respect to nucleotide sequences of the synthesized group of polynucleotides.

5. The method of claim 4, further comprising:

adding a first sequencing primer target to a first calibration region of a first synthesized polynucleotide of the synthesized group of polynucleotides to produce a modified first synthesized polynucleotide, the first sequencing primer target having a first extender sequence with a first number of nucleotides; and adding a second sequencing primer target to a second calibration region of a second synthesized polynucleotide of the synthesized group of polynucleotides to produce a modified second synthesized polynucleotide, the second sequencing primer target having a second extender sequence with a second number of nucleotides different from the first number of nucleotides.

6. The method of claim 5, wherein:

a first modified calibration region of the modified first synthesized polynucleotide includes the first extender sequence and a number of nucleotides of the first calibration region; and a second modified calibration region of the modified second synthesized polynucleotide includes the second extender sequence and a number of nucleotides of the second calibration region.

7. The method of claim 1, further comprising:

synthesizing, by the polynucleotide synthesizer, a modified polynucleotide based at least partly on the modified polynucleotide sequence.

8. The method of claim 1, wherein the group of polynucleotides includes deoxyribonucleic acid (DNA) or ribonucleic acid (RNA).

9. The method of claim 1, wherein:

individual polynucleotide sequences of the plurality of polynucleotide sequences include first regions of nucleotides that encode individual portions of digital data and second regions of polynucleotide sequences that include a file identifier corresponding to the digital data; and the calibration region of each of the plurality of polynucleotide sequences comprises at least a portion of the nucleotides included in the second regions.

10. The method of claim 9, wherein determining the number of individual polynucleotide sequences of the plurality of polynucleotide sequences having the same nucleotide located in the one or more positions of the calibration regions of the number of polynucleotides includes:

determining that a first file identifier of a first polynucleotide sequence of a one of the plurality of polynucleotide sequences and a second file identifier of a second polynucleotide sequence of a one of the plurality of polynucleotides sequences is the same.

11. A method comprising:

generating polynucleotide data indicating a polynucleotide sequence including a payload and a file identifier, the payload encoding a segment of digital data and the file identifier being associated with the digital data;

determining that a position located in a calibration region of the polynucleotide sequence has a same nucleotide as the same position located in additional calibration regions of at least a threshold number of additional polynucleotide sequences, the calibration region and the additional calibration regions including a sequence of nucleotides used by a sequencing machine during a calibration process of the sequencing machine;

modifying a portion of the polynucleotide data corresponding to the calibration region of the polynucleotide to produce a modified polynucleotide sequence having a modified calibration region such that less than the threshold number of the calibration regions include the same nucleotide at the same position; and providing the modified polynucleotide sequence to a polynucleotide synthesizer.

12. The method of claim 11, further comprising:

generating a plurality of segments of the digital data;

encoding individual segments of the plurality of segments of the digital data as polynucleotide sequence data for the payload; and generating additional polynucleotide data indicating a plurality of polynucleotide sequences, the plurality of polynucleotide sequences including the polynucleotide and individual polynucleotides of the plurality of polynucleotides including one of the individual sequences of nucleotides and the file identifier.

13. The method of claim 11, wherein modifying the calibration region includes modifying the polynucleotide data to add one or more nucleotides to at least one of a 5' end of the polynucleotide sequence or a 3' end of the polynucleotide sequence to produce the modified calibration region.

14. The method of claim 11, wherein the sequencing machine determines a sequence of the polynucleotide by:

attaching the polynucleotide to a surface of a flow cell;

producing a cluster of the polynucleotide on the surface of the flow cell by replicating the polynucleotide at a location of the surface of the flow cell;

attaching a fluorophore-bound nucleotide to complementary nucleotides at a position of individual polynucleotides of the cluster;

applying energy to the fluorophore;

capturing one or more images of the surface of the flow cell after applying energy to the fluorophore;

performing an analysis of the one or more images to determine wavelengths emitted by different locations of the surface of the flow cell; and determining, based at least partly on the analysis, a type of nucleotide at the position based on a distribution of wavelengths of electromagnetic radiation emitted by the fluorophore.

15. The method of claim 11, wherein modifying the portion of the polynucleotide data corresponding to the calibration region of the polynucleotide includes modifying an order of the nucleotides included in the calibration region.

16. A system comprising:
a processor;
a memory in communication with the processing unit, the memory storing computer-readable instructions that when executed by the processor perform operations comprising:
performing an analysis of nucleotide sequence data of a plurality of polynucleotide sequences, wherein individual ones of the plurality of polynucleotide sequences include calibration regions comprising a sequence of nucleotides used by a sequencing machine during a calibration process of the sequencing machine and payload regions that encode a segment of digital data;
determining, based at least partly on the analysis, that a likelihood of an error occurring during the calibration process of the sequencing machine while sequencing polynucleotides with nucleotide sequences indicated by the plurality of polynucleotide sequences is at least a threshold probability;
modifying the calibration regions of at least a portion of the plurality of polynucleotide sequences to produce a modified plurality of polynucleotide sequences having modified calibration regions such that the likelihood of an error occurring during the calibration process of the sequencing machine while sequencing polynucleotides with nucleotide sequences indicated by the modified plurality of polynucleotide sequences is below the threshold probability; and
providing the modified plurality of polynucleotide sequences to a polynucleotide synthesizer.

17. The system of claim 16, wherein individual sequences of the plurality of polynucleotide sequences include:
a file identifier region that encodes a file identifier associated with the digital data; and
an individual calibration region that includes at least a portion of the file identifier region.

18. The system of claim 16, wherein the operations further comprise:
determining changes between a calibration region of a polynucleotide sequence of the plurality of polynucleotide sequences and a modified calibration region of a modified polynucleotide sequence of the modified plurality of polynucleotide sequencers; and
generating a data structure that stores the changes.

19. The system of claim 18, wherein the operations further comprise:
receiving a request for the digital data;
obtaining sequence data from the sequencing machine, the sequence data including a sequence of nucleotides;
determining that the sequence of nucleotides corresponds to the modified plurality of polynucleotide sequences;
accessing the data structure to determine the changes;
generating, based on the sequence data and the changes stored in the data structure, nucleotide sequence data; and
decoding the nucleotide sequence data to produce a series of bits related to a portion of the digital data.

20. The system of claim 16, wherein determining that the likelihood of an error occurring during the calibration process of the sequencing machine while sequencing polynucleotides with nucleotide sequences indicated by the plurality of polynucleotide sequences is at least the threshold probability and includes at least one of:
determining that at least a threshold number of the plurality of polynucleotide sequences have a same nucleotide located in a same position of the calibration regions of the threshold number of the plurality of polynucleotide sequences;
determining that at least the threshold number of the plurality of polynucleotide sequences have a same nucleotide located in at least a threshold number of positions of the calibration regions of the threshold number of the plurality of polynucleotide sequences; or
determining that a distribution of nucleotides located in at least one position of the calibration regions of the plurality of polynucleotide sequences is outside of a specified distribution of nucleotides.

* * * * *